(12) United States Patent
Toporsian

(10) Patent No.: US 8,795,663 B2
(45) Date of Patent: Aug. 5, 2014

(54) SOLUBLE ENDOGLIN AND USES THEREOF

(75) Inventor: Mourad Toporsian, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 13/521,849

(22) PCT Filed: Jan. 11, 2011

(86) PCT No.: PCT/US2011/020841

§ 371 (c)(1),
(2), (4) Date: Aug. 15, 2012

(87) PCT Pub. No.: WO2011/088047

PCT Pub. Date: Jul. 21, 2011

(65) Prior Publication Data

US 2013/0136745 A1    May 30, 2013

Related U.S. Application Data

(60) Provisional application No. 61/294,177, filed on Jan. 12, 2010.

(51) Int. Cl.
  C07K 16/00 (2006.01)
  C07K 16/18 (2006.01)
  A61K 39/395 (2006.01)

(52) U.S. Cl.
  USPC .................. 424/139.1; 424/130.1; 424/145.1; 530/387.1; 530/387.9; 530/388.24

(58) Field of Classification Search
  None
  See application file for complete search history.

(56) References Cited

U.S. PATENT DOCUMENTS

2007/0083334 A1  4/2007  Mintz et al.
2007/0104707 A1  5/2007  Karumanchi et al.

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Bradley et al. (2002). Limits of cooperativity in a structurally modular protein: response of the Notch ankyrin domain to analogous alanine substitutions in each repeat, J. Mol. Biol. 324:373-386.*
Bellón et al., "Identification and expression of two forms of the human transforming growth factor-beta-binding protein endoglin with distinct cytoplasmic regions," Eur. J. Immunol. 23(9):2340-2345, 1993. (Abstract only).
Fonsatti et al., "Endoglin (CD105): A Strong Candidate for Immunologic Targeting of Tumor Neovasculature in Human Malignancies," Cancer Drug Discovery and Development: Transforming Growth Factor-β in Cancer Therapy, vol. 1, Ed. Sonia B. Jakowlew, pp. 395-410, Humana Press Inc., Totowa, NJ, 2008.
Lenato et al., "Hereditary Haemorrhagic Telangiectasia (HHT): Genetic and Molecular Aspects," Curr. Pharm. Des. 12:1173-1193, 2006.
Pichuantes et al., "Mapping epitopes to distinct regions of the extracellular domain of endoglin using bacterially expressed recombinant fragments," Tissue Antigens 50(3):265-76, 1997.
ten Dijke et al., "Endoglin in angiogenesis and vascular diseases," Angiogenesis 11(1):79-89, 2008.
International Search Report (PCT/US2011/020841), dated May 25, 2011 (3 pages).
International Preliminary Report on Patentability (PCT/US2011/020841), dated Jul. 17, 2012 (4 pages).

* cited by examiner

Primary Examiner — Christine J Saoud
Assistant Examiner — Jon M Lockard
(74) Attorney, Agent, or Firm — Clark & Elbing LLP; Kristina Bieker-Brady

(57) ABSTRACT

The invention provides isolated soluble endoglin polypeptides, nucleic acids encoding soluble endoglin polypeptides, antibodies that specifically bind soluble endoglin polypeptides, and kits containing these materials. The invention also provides methods for treating or decreasing the likelihood of developing a soluble endoglin-mediated disorder in a subject requiring the administration of an agent capable of reducing the expression or biological activity of a soluble endoglin polypeptide and methods for treating or decreasing the likelihood of developing a soluble endoglin-preventive disorder in a subject requiring the administration of a soluble endoglin polypeptide or a nucleic acid encoding the soluble endoglin polypeptide. The invention further provides methods for the diagnosis of a soluble endoglin-mediated disorder or a soluble endoglin-preventive disorder and methods for identifying a compound to treat a soluble endoglin-mediated or a soluble endoglin-preventive disorder.

4 Claims, 9 Drawing Sheets

Figure 1 sEng cDNA sequence (1683 bases)

ATG start site (Position 1) - TAA Stop codon (position 1335)

<u>ATG</u>gaccgcggcacgctccctctggctgttgccctgctgctggccagctgcagcctcagccccacaagtcttgcagaaa
cagtccattgtgaccttcagcctgtgggccccgagaggggcgaggtgacatataccactagccaggtctcgaagggctgc
gtggctcaggcccccaatgccatccttgaagtccatgtcctcttcctggagttcccaacgggcccgtcacagctggagctga
ctctccaggcatccaagcaaaatggcacctggccccgagaggtgcttctggtcctcagtgtaaacagcagtgtcttcctgca
tctccaggccctgggaatcccactgcacttggcctacaattccagcctggtcaccttccaagagcccccgggggtcaacac
cacagagctgccatccttccccaagacccagatccttgagtgggcagctgagaggggcccccatcacctctgctgctgagc
tgaatgaccccagagcatcctcctccgactgggccaagcccaggggtcactgtccttctgcatgctggaagccagccag
gacatgggccgcacgctcgagtggcggccgcgtactccagccttggtccggggctgccacttggaaggcgtggccggc
cacaaggaggcgcacatcctgagggtcctgccgggccactcggccgggccccggacggtgacggtgaaggtggaact
gagctgcgcacccggggatctcgatgccgtcctcatcctgcagggtccccctacgtgtcctggctcatcgacgccaacc
acaacatgcagatctggaccactggagaatactccttcaagatctttccagagaaaaacattcgtgcttcaagctcccaga
cacacctcaaggcctcctgggggaggcccggatgctcaatgccagcattgtggcatccttcgtggagctaccgctggcca
gcattgtctcacttcatgcctccagctgcggtggtaggctgcagacctcacccgcaccgatccagaccactcctcccaagg
acacttgtagcccggagctgctcatgtccttgatccagacaaagtgtgccgacgacgccatgaccctggtactaaagaaag
agcttgtcgcgcatttgaagtgcaccatcacgggcctgaccttctgggaccccagctgtgaggcagaggacaggggtgac
aagtttgtcttgcgcagtgcttactccagctgtggcatgcaggtgtcagcaagtatgatcagcaatgaggcggtggtcaatat
cctgtcgagctcatcaccacagcgggtgagatggacagtcacgtgc
<u>TAA</u>cccacctggcccaggggctgctgctgggccggggcctcttcctggcctgggagggagcaggcctcgggaaact
cctggcaagccatgtgtgtctggaatgcctcggtctcccttctgtatgaccggagcaggactgctgagggtgacgctctcg
gtctctcaagtcagagggcttagcacatactggctgtgtggccttgggcaagtcactttagttttctgggcccaaaggtggcc
taagaaaggactctgcgccacagggtgcttctgggcagccaatgaggtgctgtgtggaagctcttcacacagcctggcag
ctggtgcctccttgataaatattagtttaa Note: This sequence information does not include the 5'untranslated region (UTR).

sEng amino acid sequence (1-444)

mdrgtlplavalllascslsptslaetvhcdlqpvgpergevtyttsqvskgcvaqapnailevhvlflefptgpsqleltlq
askqngtwprevllvlsvnssvflhlqalgiplhlaynsslvtfqeppgvnttelpsfpktqilewaaergpitsaaelndp
qsillrlgqaqgslsfcmleasqdmgrtlewrprtpalvrgchlegvaghkeahilrvlpghsagprtvtvkvelscapg
dldavlilqgppyvswlidanhnmqiwttgeysfkifpeknirgfklpdtpqgllgearmlnasivasfvelplasivslh
asscggrlqtspapiqttppkdtcspellmsliqtkcaddamtlvlkkelvahlkctitgltfwdpsceaedrgdkfvlrsa
ysscgmqvsasmisneavvnilsssspqrvrwtvtc

Figure 2
A
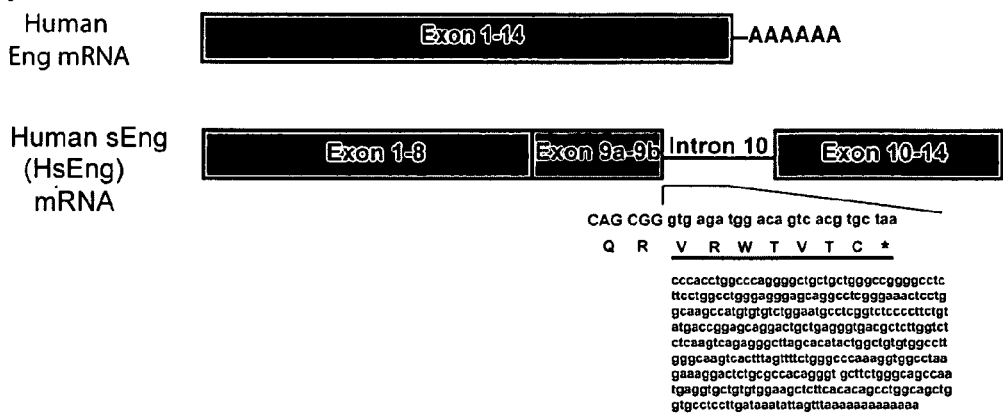
B
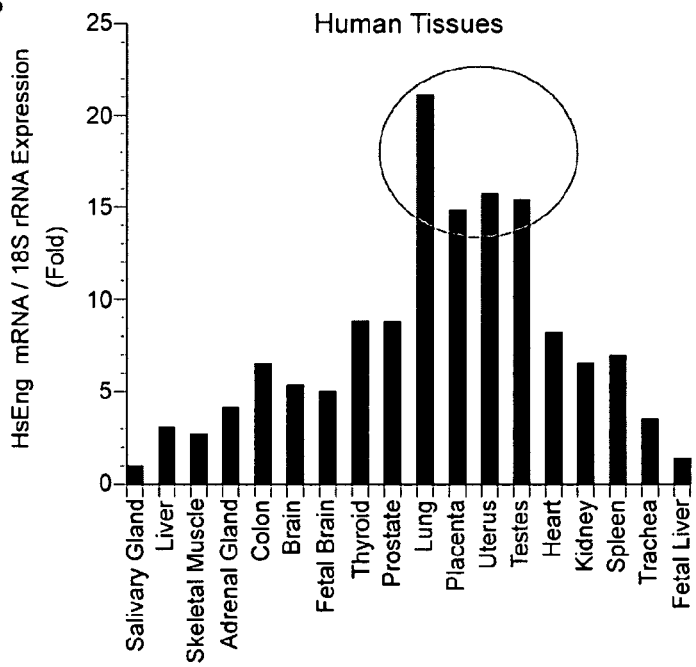

Figure 3
A
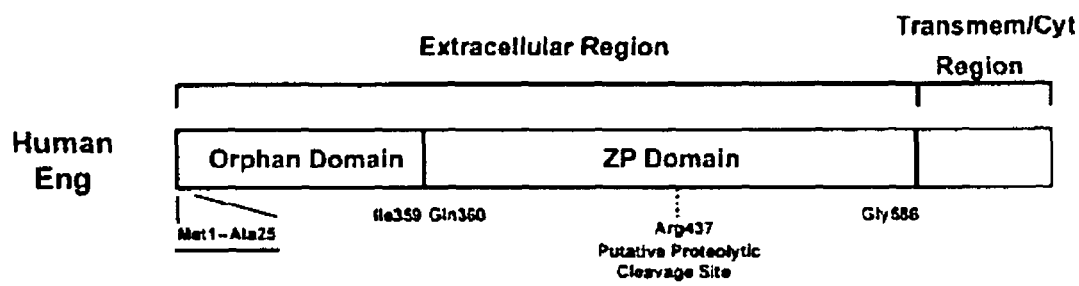
B
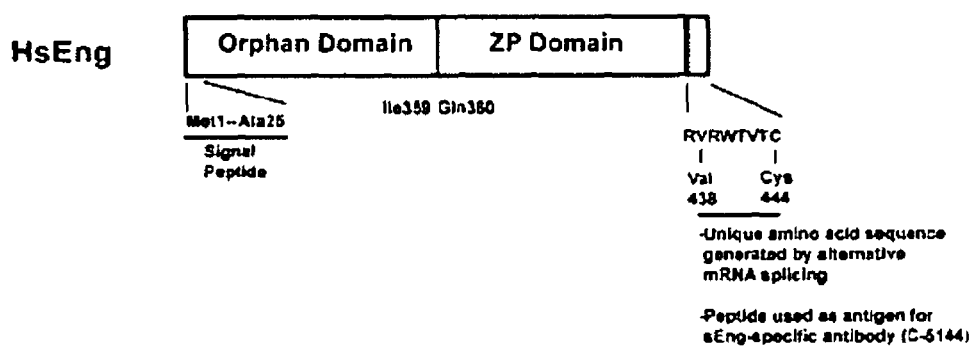
C
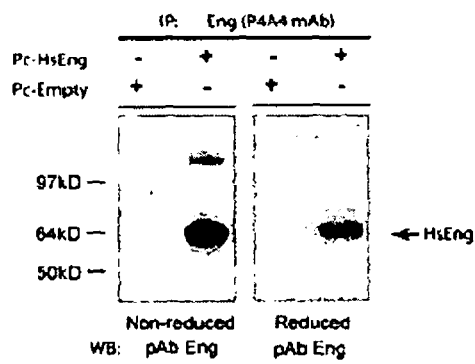
D
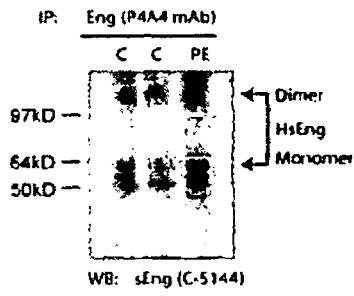

Figure 9
A
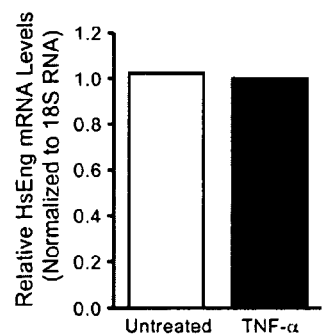
B
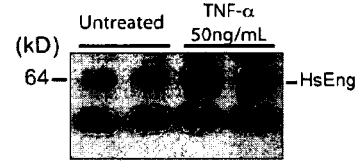
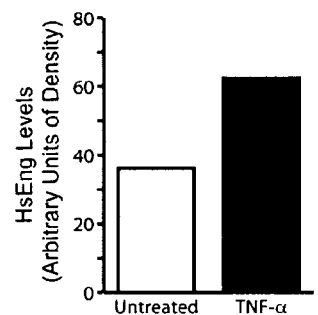

SOLUBLE ENDOGLIN AND USES THEREOF

CROSS-REFERENCE TO RELATED APPLICATIONS

This application claims the benefit of the filing date of U.S. provisional application No. 61/294,177, filed Jan. 12, 2010, herein incorporated by reference.

FIELD OF THE INVENTION

In general, this invention relates to soluble endoglin polypeptides and nucleic acids, and uses of soluble endoglin polypeptides and nucleic acids or soluble endoglin-specific compounds.

BACKGROUND OF THE INVENTION

Endoglin, also known as CD105, is a homodimeric cell membrane glycoprotein that is predominantly expressed on endothelial cells such as syncytiotrophoblasts, human umbilical vein endothelial cells (HUVEC), and on vascular endothelial cells. Endoglin shares sequence identity with betaglycan, a transforming growth factor (TGF)-β receptor type III. Endoglin has been shown to be a regulatory component of the TGF-β receptor complex, which modulates angiogenesis, proliferation, differentiation, and apoptosis. Endoglin also binds several other members of the TGF-β superfamily including activin-A, bone morphogenic protein (BMP)-2, and BMP-7. In particular, endoglin binds TGF-β1 and TGF-β3 with high affinity and forms heterotrimeric associations with the TGF-β signaling receptors types I and II. Mutations in the coding region of the endoglin gene are responsible for haemorrhagic telangiectasia type 1 (HHT1), a dominantly inherited vascular disorder characterized by multisystemic vascular dysplasia and recurrent hemorrhage.

A soluble form of endoglin was previously identified and found to interfere with TGF-β1 signaling and endothelial nitric oxide synthase (eNOS) activation in endothelial cells, thereby disrupting mechanisms necessary for maintenance of vascular health. Soluble endoglin was found to be present at increased levels in patients with metastatic breast and colorectal cancer. It has also been shown that patients having pre-eclampsia produce large quantities of soluble endoglin and that soluble endoglin contributes to the pathogenesis of pre-eclampsia.

There is a need for methods of treating and diagnosing subjects at risk for or having a soluble endoglin-mediated disorder (e.g., eclampsia and pre-eclampsia) or a soluble endoglin-preventive disorder (e.g., disorders characterized by increased TGF β expression or biological activity).

SUMMARY OF THE INVENTION

We have discovered a form of soluble endoglin produced by alternative splicing of the endoglin precursor mRNA. We have isolated this previously unrecognized mRNA transcript of endoglin from human tissue and discovered that it encodes a stable and soluble (secreted) protein. This soluble form of endoglin exists predominantly as a monomer and is able to modulate TGF-β/BMP signaling. The soluble endoglin described herein includes a unique C-terminal amino acid sequence of amino acids 437-444 of RVRWTVTC (SEQ ID NO: 1) or amino acids 438-444 of VRWTVTC (SEQ ID NO: 2) and has a soluble endoglin biological activity. The unique C-terminal amino acid sequences and the complete amino acid and nucleic acid sequences of the alternatively spliced mRNA transcript of soluble endoglin are shown in FIGS. 2A, 3B, and 1, respectively.

The unique amino acid sequences incorporated into soluble endoglin as a result of alternative splicing can be used to generate soluble endoglin-specific compounds (e.g., an antibody, a small molecule inhibitor, or a small inhibitory RNA, such as miRNA or siRNA) that specifically target, bind, or modulate the expression or activity of this form of soluble endoglin. For example, antibodies can be used to specifically detect or modulate the biological activity or expression of this protein in a number of soluble endoglin-mediated diseases including but not limited to pregnancy related hypertensive disorders (e.g., pre-eclampsia, eclampsia, gestational hypertension, chronic hypertension, HELLP syndrome, and pregnancy with a SGA infant), pulmonary hypertension, and malaria. In addition, elevated soluble endoglin levels have been detected in cancers, in senior patients with Alzheimer's disease and in patients with cerebral arteriovenous malformations, and individuals with suspected left ventricular dysfunction also display elevated soluble endoglin levels suggesting that circulating levels of this protein may be a sensitive measure of elevated left heart filling pressures. Moreover, soluble endoglin levels are elevated in patients with diabetes having retinopathy and/or a high probability of 10-year cardiovascular risk, as well as in patients with diabetes and hypertension who have three or more damaged target organs (e.g., heart, vessels, and kidney). Compounds that reduce, decrease, or inhibit the expression levels or biological activity of soluble endoglin can be used to treat any of the above endoglin-mediated diseases.

Alternatively, isolated soluble endoglin polypeptides and fragments, derivatives, or analogs thereof, and agents that increase the expression or a biological activity of a soluble endoglin polypeptide of the invention may be used to treat a subject having a soluble endoglin-preventive disorder such as those characterized by factors (e.g. increased TGF-β levels or activity) or events (e.g. fibrosis, angiogenesis, immune activation) that contribute to the disorder and/or that can be inhibited or modulated by soluble endoglin. Examples include fibrotic disorders of internal organs and the scarring of skin where TGF-β is a significant contributor, disorders characterized by excessive angiogenesis (e.g. hemangiomas, pulmonary capillary hemangiomatosis) or abnormal growth of blood vessel such as cancer (e.g., cancer of the breast, prostate, colon, lung, head and neck, liver, kidney, renal system, and endometrium) and inflammatory and immune disorders.

Accordingly, in a first aspect, the invention features an isolated soluble endoglin polypeptide that includes a sequence that is at least 85% identical to VRWTVTC (SEQ ID NO: 2) and has a soluble endoglin biological activity. In one embodiment, the sequence that is at least 85% identical to SEQ ID NO: 2 is located at the C-terminus of the soluble endoglin polypeptide. In another embodiment the soluble endoglin polypeptide includes the sequence of SEQ ID NO: 2, desirably at the C-terminus of the soluble endoglin.

In various embodiments, the isolated soluble endoglin polypeptide includes or consists of an amino acid sequence that is at least 98%, 99%, or 100% identical to SEQ ID NO: 3. The soluble endoglin polypeptide can include fragments of soluble endoglin, for example, fragments that include a total of at least 100, 200, 250, 300, 350, 400, or 444 amino acids. The soluble endoglin polypeptide, or fragments thereof, can further include an additional amino acid sequence at the N- or C-terminus, which can be at least 5, 10, 15, 20, 25 amino acids or more.

In various embodiments, the soluble endoglin polypeptide biological activity is selected from the group consisting of: the ability to bind to TGF-β1, the ability to bind to TGF-β3, the ability to bind to activin-A, the ability to bind to bone morphogenic protein (BMP)-2, the ability to bind to BMP-7, the ability to bind to BMP-9, the ability to bind to BMP receptor II, the ability to bind TGF-β receptor I, the ability to bind to TGF-β receptor II, the ability to reverse or inhibit angiogenesis, the ability to reduce or inhibit Smad 2/3-dependent transcriptional activation, and the ability to inhibit endothelial nitric oxide synthase activation.

The isolated soluble endoglin polypeptide can further include one or more modifications selected from the group consisting of: acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, S-nitrosylation, disulfide bond formation, demethylation, formation of cysteine, formation of sulfonic, sulfenic, or sulfinic acid, formation of pyroglutamate, formylation, gamma-carboxylation, glycosylation, GPI-anchor formation, hydroxylation, iodination, methylation, myristoylation, oxidation, pegylation, phosphorylation, prenylation, racemization, selenoylation, sulfation, transfer-RNA mediated addition of amino acids, ubiquitination, D-isomerization, derivitization of water soluble polymers, addition of a detectable label, and conjugation of another protein or therapeutic compound. In one embodiment, the modification includes glycosylation, oxidation, or s-nitrosylation.

In another embodiment, the invention features an antibody, or antibody binding fragment thereof, that specifically binds to a soluble endoglin polypeptide, where the antibody, or antibody-binding fragment, binds to an epitope comprising a sequence that is at least 85% identical to VRWTVTC (SEQ ID NO: 2), or a fragment thereof. Desirably, the epitope fragment is at least 3 amino acids, 4 amino acids, 5 amino acids, or 6 amino acids. In one embodiment, the antibody or antibody-binding fragment binds to an epitope that includes SEQ ID NO: 2. In another embodiment, the antibody or antibody-binding fragment competes with the antibody C-5144 for binding to soluble endoglin.

In various embodiments, the antibody, or antibody binding fragment inhibits one of more of the following activities of soluble endoglin: the ability to bind to TGF-β1, the ability to bind to TGF-β3, the ability to bind to activin-A, the ability to bind to bone morphogenic protein (BMP)-2, the ability to bind to BMP-7, the ability to bind to BMP-9, the ability to bind to BMP receptor II, the ability to bind TGF-β receptor I, the ability to bind to TGF-β receptor II, the ability to reverse or inhibit angiogenesis, the ability to reduce or inhibit Smad 2/3-dependent transcriptional activation, and the ability to inhibit endothelial nitric oxide synthase activation.

The antibody, or fragment thereof, can be a monoclonal antibody, a chimeric, a humanized, a human antibody, an antibody that lacks an Fc portion or is a $F(ab')_2$, a Fab, or an Fv structure.

In various embodiments, the antibody or antibody binding fragment is in a pharmaceutically acceptable carrier.

In another embodiment, the invention features an isolated nucleic acid molecule that includes a sequence that is at least 95% identical to the sequence of SEQ ID NO: 4 and that includes a sequence that encodes an amino acid sequence that has a soluble endoglin biological activity wherein the amino acid sequence includes a sequence that is at least 85% identical to VRWTVTC (SEQ NO: 2).

In addition embodiments, the sequence that encodes an amino acid sequence that is at least 85% identical to SEQ ID NO: 2 is located at the 3' terminus of the nucleic acid molecule. In various embodiments, the nucleic acid includes a sequence that encodes the amino acid sequence of SEQ ID NO: 2.

In another aspect, the invention features an isolated inhibitory nucleic acid molecule, that includes at least one strand that is complementary to a nucleic acid sequence that encodes an amino acid sequence that is at least 85% identical to VRWTVTC (SEQ ID NO: 2), or a fragment thereof, and wherein the inhibitory nucleic acid molecule reduces or inhibits the expression or a biological activity of a soluble endoglin polypeptide. In one embodiment, the inhibitory nucleic acid molecule has at least one strand that is complementary to a nucleic acid sequence that encodes the amino acid sequence of SEQ ID NO: 2. In another embodiment, the isolated inhibitory nucleic acid molecule reduces or inhibits a biological activity of a soluble endoglin that is selected from the group consisting of: the ability to bind to TGF-β1, the ability to bind to TGF-β3, the ability to bind to activin-A, the ability to bind to bone morphogenic protein (BMP)-2, the ability to bind to BMP-7, the ability to bind to BMP-9, the ability to bind to BMP receptor II, the ability to bind TGF-β receptor I, the ability to bind to TGF-β receptor II, the ability to reverse or inhibit angiogenesis, the ability to reduce or inhibit Smad 2/3-dependent transcriptional activation, and the ability to inhibit endothelial nitric oxide synthase activation.

In various embodiments, the isolated inhibitory nucleic acid molecule is a double-stranded RNA, a small interfering RNA (siRNA) or a micro RNA (miRNA). The siRNA can be between 17 to 25 nucleotides in length. In another embodiment, the isolated inhibitor nucleic acid molecule is single-stranded DNA or an antisense nucleobase oligomer.

In another aspect, the invention features a method of treating or decreasing the likelihood of developing a soluble endoglin-mediated disorder in a subject, that includes the step of administering to the subject an agent capable of reducing the expression or biological activity of a soluble endoglin polypeptide, wherein the soluble endoglin polypeptide comprises a sequence that is at least 85% identical to VRWTVTC (SEQ ID NO: 2). In one embodiment, the administering results in a reduction of the expression or biological activity of a soluble endoglin polypeptide that includes the sequence of SEQ ID NO: 2. In another embodiment, the administering results in a reduction of the expression or biological activity of a soluble endoglin polypeptide that includes an amino acid sequence that is at least 98% identical to the corresponding amino acid sequence in SEQ ID NO: 3. The biological activity of the soluble endoglin polypeptide can include the ability to bind to TGF-β1, the ability to bind to TGF-β3, the ability to bind to activin-A, the ability to bind to bone morphogenic protein (BMP)-2, the ability to bind to BMP-7, the ability to bind to BMP-9, the ability to bind to BMP receptor II, the ability to bind TGF-β receptor I, the ability to bind to TGF-β receptor II, the ability to reverse or inhibit angiogenesis, the ability to reduce or inhibit Smad 2/3-dependent transcriptional activation, and the ability to inhibit endothelial nitric oxide synthase activation.

In various embodiments of the above aspect, the agent is a purified antibody or antibody binding fragment thereof that specifically binds to a soluble endoglin polypeptide, where the antibody or antibody-binding fragment binds to an epitope that includes a sequence that is at least 85% identical to SEQ ID NO: 2, or a fragment thereof. Desirably, the epitope fragment is at least 3 amino acids, 4 amino acids, 5 amino acids, or 6 amino acids. In one embodiment, the antibody or antibody-binding fragment binds to an epitope that includes SEQ ID NO: 2. In another embodiment, the antibody or antibody-binding fragment competes with the antibody C-5144 for binding to soluble endoglin. The antibody, or fragment thereof, can be a monoclonal antibody, a chimeric, a humanized, a human antibody, an antibody that lacks an Fc portion or is a F(ab')$_2$, a Fab, or an Fv structure. In various embodiments, the antibody or antibody binding fragment is in a pharmaceutically acceptable carrier.

In another embodiment of the above aspect, the agent is an inhibitory nucleic acid molecule that includes at least one strand that is complementary to a nucleic acid sequence that encodes an amino acid sequence that is at least 85% identical to SEQ ID NO: 2, or a fragment thereof, and wherein the inhibitory nucleic acid molecule reduces or inhibits the expression or a biological activity of a soluble endoglin polypeptide. The inhibitory nucleic acid molecule desirably has at least one strand that is complementary to a nucleic acid sequence that encodes the amino acid sequence of SEQ ID NO: 2.

In one embodiment, the inhibitory nucleic acid molecule is a double-stranded RNA, a small interfering RNA (siRNA) or a micro RNA. The siRNA can be between 17 to 25 nucleotides in length. In another embodiment, the isolated inhibitor y nucleic acid molecule is single-stranded DNA or an antisense nucleobase oligomer.

In various embodiment of the above aspect, the a soluble endoglin-mediated disorder is selected from the group consisting of: pre-eclampsia, eclampsia, gestational hypertension, chronic hypertension, HELLP syndrome, pregnancy with a smaller-for-gestational-age (SGA) infant, abruption pregnancy, pregnancy with intrauterine growth restriction, pulmonary hypertension, cancer (where soluble endoglin is elevated), and malaria. Additional non-limiting examples of soluble endoglin-mediated disorders include Alzheimer's disease, cerebral arteriovenous malformations, left ventricular dysfunction, and patients with diabetes having retinopathy and/or a high probability of 10-year cardiovascular risk, as well as patients with diabetes and hypertension who have three or more damaged target organs (e.g., heart, vessels, and kidney). Desirably, a soluble endoglin-mediated disorder is pre-eclampsia or eclampsia.

In various embodiments, the method results in at least a 10%, 20%, 30%, 40%, 50%, 60%, 70%, 80%, 90%, or more reduction in one or more symptoms of a soluble endoglin-mediated disorder. In additional embodiments, the method further includes administering one or more agents selected from the group of: an agent that increases endothelial nitric oxide synthase expression or biological activity, an agent that increases the levels of prostacyclin or prostacyclin biological activity, an agent that increases TGF-β levels or biological activity, an agent that decreases sFlt-1 expression or biological activity, an agent that increases vascular endothelial factor levels or biological activity, and an agent that increases placenta growth factor levels or biological activity.

In another aspect, the invention features a method of treating or decreasing the likelihood of developing a soluble endoglin-preventive disorder in a subject, that includes the step of administering to the subject an isolated soluble endoglin polypeptide having a soluble endoglin biological activity and comprising a sequence that is at least 85% identical to VRWTVTC (SEQ ID NO: 2), or an isolated nucleic acid encoding the isolated soluble endoglin polypeptide.

In one embodiment, the sequence that is at least 85% identical to SEQ ID NO: 2 is located at the C-terminus of the soluble endoglin polypeptide. In another embodiment the soluble endoglin polypeptide includes the sequence of SEQ ID NO: 2, desirably at the C-terminus of the soluble endoglin.

In various embodiments, the isolated soluble endoglin polypeptide includes or consists of an amino acid sequence that is at least 98%, 99%, or 100% identical to SEQ ID NO: 3. The soluble endoglin polypeptide can include fragments of soluble endoglin, for example, fragments that include a total of at least 100, 200, 250, 300, 350, 400, or 444 amino acids. The soluble endoglin polypeptide, or fragments thereof, can further include an additional amino acid sequence at the N- or C-terminus, which can be comprises at least 5, 10, 15, 20, 25 amino acids or more.

In additional embodiments, the soluble endoglin polypeptide biological activity is selected from the group consisting of: the ability to bind to TGF-β1, the ability to bind to TGF-β3, the ability to bind to activin-A, the ability to bind to bone morphogenic protein (BMP)-2, the ability to bind to BMP-7, the ability to bind to BMP-9, the ability to bind to BMP receptor II, the ability to bind TGF-β receptor I, the ability to bind to TGF-β receptor II, the ability to reverse or inhibit angiogenesis, the ability to reduce or inhibit Smad 2/3-dependent transcriptional activation, and the ability to inhibit endothelial nitric oxide synthase activation.

The isolated soluble endoglin polypeptide can further include one or more modifications selected from the group consisting of: acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, S-nitrosylation, disulfide bond formation, demethylation, formation of cysteine, formation of sulfonic, sulfenic, or sulfinic acid, formation of pyroglutamate, formylation, gamma-carboxylation, glycosylation, GPI-anchor formation, hydroxylation, iodination, methylation, myristoylation, oxidation, pegylation, phosphorylation, prenylation, racemization, selenoylation, sulfation, transfer-RNA mediated addition of amino acids, ubiquitination, D-isomerization, derivitization of water soluble polymers, addition of a detectable label, and conjugation of another protein or therapeutic compound. In one embodiment, the modification includes glycosylation or s-nitrosylation.

In various embodiments, the soluble endoglin-preventive disorder includes a disorder characterized by factors (e.g. increased soluble endoglin or TGF-β1 or 3 levels or activity) or events (e.g. fibrosis, angiogenesis, immune activation) that contribute to the disorder and/or that can be inhibited or modulated by soluble endoglin. Examples include fibrotic disorders of internal organs and the scarring of skin where TGF-β is a significant contributor, disorders characterized by excessive angiogenesis (e.g. hemangiomas, pulmonary capillary hemangiomatosis) or abnormal growth of blood vessel such as cancer (e.g., cancer of the breast, prostate, colon, lung, head and neck, liver, kidney, renal system, and endometrium) and inflammatory and immune disorders.

In various embodiment of the above aspect, the soluble endoglin-preventive disorder is a disorder characterized by increased TGF-β (e.g., TGF β1 or TGFβ3) or TGF β receptor levels. In another embodiment, the soluble endoglin-preventive disorder is cancer, and the method further comprises administering to the subject one or more agents selected from the group consisting of: a chemotherapeutic agent, an angiogenesis inhibitor, and an anti-proliferative compound.

Desirably, for any of the above therapeutic aspects, the subject is a mammal, preferably a human.

In another aspect, the invention features a method of diagnosing a subject as having, or having the predisposition to develop, a soluble endoglin-mediated disorder or a soluble endoglin-preventive disorder, wherein the method includes the steps of:

(a) measuring the level of a soluble endoglin polypeptide having a soluble endoglin biological activity and including a sequence that is at least 85% identical to VRWTVTC (SEQ ID NO: 2) in a sample from a subject;

(b) measuring the level of the soluble endoglin polypeptide in a control sample; and (c) comparing the level of the soluble endoglin polypeptide in the subject to the level of the soluble endoglin polypeptide in the control sample; wherein an increase in the level of the soluble endoglin polypeptide in the subject as compared to the level of the soluble endoglin polypeptide in the control sample diagnoses the subject as having, or having a disposition for developing, a soluble endoglin-mediated disorder, or wherein a decrease in the level of the soluble endoglin polypeptide in the subject as compared to the level of the soluble endoglin polypeptide in the control sample diagnosis the subject as having, or having a disposition for developing, a soluble endoglin-preventive disorder.

In one embodiment, the sequence that is at least 85% identical to SEQ ID NO: 2 is located at the C-terminus of the soluble endoglin polypeptide. In another embodiment, the soluble endoglin polypeptide comprises an amino acid sequence that is at least 98% identical to SEQ ID NO: 3.

In various embodiments, the measuring in step (a) or step (b) is performed using an antibody or antibody binding fragment thereof that specifically binds to a soluble endoglin polypeptide, wherein the antibody or antibody-binding fragment binds to an epitope comprising a sequence that is at least 85% identical to SEQ ID NO: 2, or a fragment thereof. Desirably, the fragment is at least 3 amino acids, 4 amino acids, 5 amino acids, or 6 amino acids. In one embodiment, the antibody or antibody-binding fragment binds to an epitope that includes SEQ ID NO: 2. In another embodiment, the antibody or antibody-binding fragment competes with the antibody C-5144 for binding to soluble endoglin.

In one embodiment, the method includes the use of an immunoassay. In another embodiment, the control sample is a prior sample from the subject. The sample from the subject or the control sample can be a bodily fluid (e.g., urine, amniotic fluid, blood, serum, or plasma), cell, or a tissue sample.

In another aspect, the invention features a kit that includes: (a) an antibody or antibody binding fragment thereof that reduces the levels or biological activity of a soluble endoglin polypeptide comprising a sequence that is at least 85% identical to VRWTVTC (SEQ ID NO: 2), wherein the antibody or antibody binding fragment thereof specifically binds to an epitope that includes a sequence that is at least 85% identical to SEQ ID NO: 2, or a fragment thereof; and (b) instructions for administering that antibody of (a) to a subject having a soluble endoglin-mediated disorder.

In one embodiment, the antibody or antibody-binding fragment binds to an epitope that includes the sequence of SEQ ID NO: 2. In another embodiment, the antibody is a monoclonal antibody or any antibody described herein.

In another aspect, the invention features a kit that includes: (a) an inhibitory nucleic acid molecule that reduces the levels or biological activity of a soluble endoglin polypeptide comprising a sequence that is at least 85% identical to VRWTVTC (SEQ ID NO: 2), wherein the inhibitory nucleic acid molecule includes at least one strand that is complementary to a nucleic acid sequence that encodes an amino acid sequence that is at least 85% identical to VRWTVTC (SEQ ID NO: 2), and (b) instructions for administering the inhibitory nucleic acid molecule of (a) to a subject having a soluble endoglin-mediated disorder.

In another embodiment of the above aspect, the inhibitory nucleic acid molecule includes at least one strand that is complementary to a nucleic acid sequence that encodes an amino acid sequence that is at least 85% identical to SEQ ID NO: 2, and wherein the inhibitory nucleic acid molecule reduces or inhibits the expression or a biological activity of a soluble endoglin polypeptide. The inhibitory nucleic acid molecule desirably has at least one strand that is complementary to a nucleic acid sequence that encodes the amino acid sequence of SEQ ID NO: 2.

In one embodiment, the inhibitory nucleic acid molecule is a double-stranded RNA, a small interfering RNA (siRNA) or a micro RNA. The siRNA can be between 17 to 25 nucleotides in length. In another embodiment, the isolated inhibitor nucleic is single-stranded DNA or an antisense nucleobase oligomer.

In various embodiments of either of the above aspects, the kit further includes one or more agents selected from the group of: an agent that increases endothelial nitric oxide synthase expression or biological activity, an agent that increases the levels of prostacyclin or prostacyclin biological activity, an agent that increases TGF-β levels or biological activity, an agent that decreases sFlt-1 expression or biological activity, an agent that increases vascular endothelial factor levels or biological activity, and an agent that increases placenta growth factor levels or biological activity.

In another aspect, the invention features a kit that includes (a) an isolated soluble endoglin polypeptide, wherein the soluble endoglin polypeptide has a soluble endoglin biological activity and includes a sequence that is at least 85% identical to VRWTVTC (SEQ ID NO: 2) or a nucleic acid encoding the soluble endoglin polypeptide; and (b) instructions for administering the soluble endoglin polypeptide or the nucleic acid encoding the soluble endoglin polypeptide to a subject having a soluble endoglin-preventive disorder. In one embodiment, the sequence that is at least 85% identical to SEQ ID NO: 2 is located at the C-terminus of the soluble endoglin polypeptide. In another embodiment the soluble endoglin polypeptide includes the sequence of SEQ ID NO: 2, desirably at the C-terminus of the soluble endoglin.

In various embodiments, the isolated soluble endoglin polypeptide includes or consists of an amino acid sequence that is at least 98%, 99%, or 100% identical to SEQ ID NO: 3. The soluble endoglin polypeptide can include fragments of soluble endoglin, for example, fragments that include a total of at least 100, 200, 250, 300, 350, 400, or 444 amino acids. The soluble endoglin polypeptide, or fragments thereof, can further include an additional amino acid sequence at the N- or C-terminus, which can be comprises at least 5, 10, 15, 20, 25 amino acids or more.

In various embodiments, the kit further includes one or more agents selected from the group of: a chemotherapeutic agent, an angiogenesis inhibitor, and an anti-proliferative compound.

By "binding" is meant a non-covalent or a covalent interaction, preferably non-covalent, that holds two molecules together. For example, two such molecules could be a ligand and its receptor, an enzyme and an inhibitor of that enzyme, an enzyme and its substrate, or an antibody and an antigen. Non-covalent interactions include, but are not limited to, hydrogen bonding, ionic interactions among charged groups, van der Waals interactions, and hydrophobic interactions among non-polar groups. One or more of these interactions can mediate the binding of two molecules to each other. Binding may exhibit discriminatory properties such as specificity or selectivity.

By "tumor" or "cancer" is meant both benign and malignant growths of cancer. The cancer can be a non-solid tumor (e.g., a tumor that grows within the blood stream) or a solid tumor, which refers to one that grows in an anatomical site outside the bloodstream (in contrast, for example, to blood-borne tumors, such as lymphomas and leukemia) and requires the formation of small blood vessels and capillaries to supply nutrients, etc., to the growing tumor mass. Examples of solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organ, bladder, skin, sarcomas, brain tumors, and bone tumors. The methods and compositions of the invention may be used to treat or decrease the likelihood of developing any type of cancer encompassed by this definition of "cancer."

By "chemotherapeutic agent" is meant a chemical that may be used to destroy a cancer cell, or to slow, arrest, or reverse the growth of a cancer cell. Chemotherapeutic agents include, without limitation, anastrozole, asparaginase, azacitidine, bevacizumab, dicalutamide, bleomycin, bortezomib, busulfan carmustine (commonly referred to as BCNU), capecitabine, carboplatin, cetuximab, chlorambucil, cisplatin, cladribine (commonly referred to as 2-CdA), CPT11, cyclophosphamide, cytarabine (commonly referred to as Ara-C), dacarbazine, dasatinib, daunorubicin, dexamethasone, docetaxel, doxorubicin (commonly referred to as Adriamycin), epirubicin, erlotinib, exemestane, etoposide, fludarabine, 5-fluorouracil (commonly referred to as 5FU), gefitinib, gemcitabine, goserelin, hydroxyurea, idarubicin, ifosfamide, imatinib, interferon-7 (native or recombinant), irinotecan, lapatinib, letrozole, levamisole, lomustine (commonly referred to as CCNU), mechlorethamine (commonly referred to as nitrogen mustard), melphalan, mercaptopurine, methotrexate, mitomycin, mitoxantrone, oxaliplatin, paclitaxel, pemetrexed, pentostatin, prednisone, procarbazine, rituximab, sorafenib, sunitinib, tamoxifen, taxol-related compounds, temozolomide, 6-thioguanine, topotecan, trastuzumab, triptorelin, vinblastine, vincristine, and vinorelbine.

By "compound" is meant any small molecule chemical compound (peptidyl or non-peptidyl), antibody, nucleic acid molecule, polypeptide, or fragments thereof. Compounds particularly useful for methods of treating or decreasing the likelihood of developing a soluble endoglin-mediated disorder preferably decrease the levels (protein or mRNA levels) or a biological activity of soluble endoglin polypeptide of the invention by at least 5%, 10%, 15%, 20%, 25%, 30%, 35%, 40%, 45%, 50%, 60%, 70%, 80%, 90%, 95%, or 99% or more. Assays for measuring the biological activity of soluble endoglin are described herein or are known in the art. Compounds particularly useful for methods of treating or decreasing the likelihood of developing a soluble endoglin-preventive disorder preferable increase the levels of soluble endoglin of the invention (protein or mRNA levels) or a biological activity of soluble endoglin polypeptide of the invention by at least 5%, 10%, 15%, 20%, 25%, 30%, 35%, 40%, 45%, 50%, 55%, 60%, 70%, 80%, 90%, 95%, or 99% or more.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495, 1975, or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628, 1991 and Marks et al., *J. Mol. Biol.* 222:581-597, 1991, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. U.S.A.* 81:6851-6855, 1984).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522-525, 1986; Riechmann et al., *Nature* 332: 323-329, 1988; and Presta, *Curr. Opin. Struct. Biol.* 2:593-596, 1992.

The term "human antibody" or "fully human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) Handbook of Experimental Pharmacology 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e., humanized antibodies).

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In a preferred embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e., same residue) or similar (i.e., amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule (e.g., Ghetie et al., *Ann. Rev. Immunol.* 18:739-766, 2000, Table 1). Antibodies with substitutions in an Fc region thereof and increased serum half-lives are also described in WO 00/42072; WO 02/060919; Shields, R. L., et al., *J. Biol. Chem.* 276(9):6591-6604, 2001; Hinton, P. R., *J. Biol. Chem.* 279(8):6213-6216, 2004). In another embodiment, the serum half-life can also be increased, for example, by attaching other polypeptide sequences. For example, antibodies of this invention or other polypeptide containing the amino acid sequences of this invention can be attached to serum albumin or a portion of serum albumin that binds to the FcRn receptor or a serum albumin binding peptide so that serum albumin binds to the antibody or polypeptide, e.g., such polypeptide sequences are disclosed in WO 01/45746. In one preferred embodiment, the serum albumin peptide to be attached comprises an amino acid sequence of DICLPRWGCLW (SEQ ID NO: 5). In another embodiment, the half-life of a Fab according to this invention is increased by these methods. See also, Dennis, M. S., et al., *J. Biol. Chem.* 277(38):35035-35043, 2002 for serum albumin binding peptide sequences.

By "double-stranded RNA (dsRNA)" is meant a ribonucleic acid molecule comprised of both a sense and an anti-sense strand. dsRNAs are typically used to mediate RNA interference.

By "endoglin" or "Eng," also known as CD105, is meant a mammalian growth factor that has endoglin biological activity (see, Fonsatti et al., *Oncogene* 22:6557-6563, 2003; Fonsatti et al., *Curr. Cancer Drug Targets* 3:427-432, 2003; and Cheifetz et al., *J. Biol. Chem.* 267:19027-19030 (1992)) and is homologous to the protein defined by any of the following GenBank Accession Numbers: AAH29080 and NP_031958 (mouse); AAS67893 (rat); NP_000109, P1781, VSP_004233, and CAA80673 (pig); and CAA50891 and AAC63386 (human); or the sequences described in U.S. Pat. No. 6,562,957. Endoglin is a homodimeric cell membrane glycoprotein which is expressed at high levels in proliferating vascular endothelial cells and in the syncytiotrophoblasts from placentas. There are two distinct isoforms of endoglin, L and S, which differ in their cytoplasmic tails by 47 amino acids. Both isoforms are included in the term endoglin as used herein. Endoglin binds to TGF-β family members and, in the presence of TGF-β, endoglin can associate with the TGF-β signaling receptors RI and RII or BMP receptor II, and potentiate the response to the growth factors. Endoglin biological activities include: binding to substrates such as TGF-β family members, such as activin-A, BMP-2, BMP-7, BMP-9, TGF-β1, and TGF-β3; induction of angiogenesis; regulation of cell proliferation, attachment, migration, and invasion; and activation of endothelial cells. Assays for endoglin biological activities are known in the art and are described in WO 07/143,023 and WO 08/030,283 (each incorporated by reference), and include without limitation ligand binding assays or Scatchard plot analysis; BrdU labeling, cell counting experiments, or quantitative assays for DNA synthesis such as $^3$H-thymidine incorporation used to measure cell proliferation; and angiogenesis assays such as those described in McCarty et al., *Intl. J. Oncol.* 21:5-10, 2002; Akhtar et al. *Clin. Chem.* 49:32-40, 2003; and Yamashita et al, *J. Biol. Chem.* 269:1995-2001, 1994.

By "soluble endoglin polypeptide" or "sEng" is meant a circulating, non-membrane bound form of endoglin which includes at least a part of the extracellular portion of the endoglin protein, contains a sequence that is substantially identical (e.g., at least 70%, 71%, 72%, 73%, 74%, 75%, 80%, 81%, 82%, 83%, 84%, 85%, 90%, 95%, 96%, 97%, 98%, 99%, or 100% identical) to the sequence of VRWTVTC (SEQ ID NO: 2), and has a soluble endoglin biological activity. In one embodiment, the soluble endoglin polypeptide contains the sequence of SEQ ID NO: 1. Desirable forms of soluble endoglin polypeptides contain the sequence of SEQ ID NO: 1 or SEQ ID NO: 2 and have a soluble endoglin biological activity. The forms of soluble endoglin polypeptide encompassed by this term may be produced from the alternate splicing of an endoglin precursor mRNA and may be monomeric. For example, one non-limiting example of a soluble endoglin polypeptide is depicted in FIG. 1 (cDNA and polypeptide sequences corresponding to SEQ ID NOS: 4 and 3, respectively). Non-limiting examples of soluble endoglin polypeptides of the invention contain a sequence that is substantially identical (e.g., at least 70%, 75%, 85%, 90%, 95%, or even 100% identical) to SEQ ID NO: 1 or SEQ ID NO: 2 (e.g., may contain one or two conservative mutations in the sequence of SEQ ID NO: 1 or SEQ ID NO: 2), have a soluble endoglin biological activity, and may also contain a sequence that is at least 85% identical (e.g., at least 90%, 95%, 96%, 97%, 98%, 99%, or 100% identical) to the sequence of SEQ ID NO: 3 (upon comparing an equal number of amino acids in the sequence of the soluble endoglin polypeptide to an equal number of amino acids in the sequence of SEQ ID NO: 3). Preferred soluble endoglin polypeptides contain a sequence at least 85% identical (e.g., at least 90%, 95%, 96%, 97%, 98%, 99%, or 100% identical) to SEQ ID NO: 1 or SEQ ID NO: 2 at the C-terminus Soluble endoglin polypeptides include a sequence that is substantially identical to SEQ ID NO: 2, have a soluble endoglin biological activity, and may have a total length of at least 10 amino acids (e.g., at least 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, or 444 amino acids). Soluble endoglin polypeptides of the invention may contain at least 444 amino acids. The soluble endoglin polypeptides of the invention may also contain additional amino acids sequences at the N- and/or C-terminus of the polypeptide.

The soluble endoglin polypeptides of the invention have a soluble endoglin polypeptide biological activity such as, but limited to, binding to substrates such as TGF-β family members (e.g., TGF-β1, TGF-β3, activin-A, BMP-2, BMP-7, and BMP-9), TGF-β receptors (e.g., TGF-β receptor I and TGF-β receptor II), or BMP receptor II reducing or inhibiting the activation of Smad 2/3 or Smad 2/3-dependent transcriptional activation, inhibiting the biological activity of TGF-β family members, reversing or inhibiting angiogenesis induced by TGF-β by at least 5%, 10%, 15%, 20%, 25%, 30%, 35%, 40%, 45%, 50%, 55%, 60%, 70%, 80%, 90%, or more, or inhibiting endothelial nitric oxide synthase activation. Examples of assays for measuring these activities are known in the art and described in U.S. Patent Application Publication Nos. 20060067937, 20050267021, and 20070104707 and PCT Publication Nos. WO 06/034507, WO 07/143,023, and WO 08/030,283 (each incorporated herein by reference). Soluble endoglin polypeptides may be isolated from a variety of sources, such as from mammalian tissue or cells (e.g., placental tissue or cells), or prepared by recombinant or synthetic methods. The term soluble endoglin polypeptide can also encompass modifications to the polypeptide or fragments of the soluble endoglin polypeptide, and derivatives and analogues thereof, examples of which are described below.

By "soluble endoglin nucleic acid" is meant a nucleic acid that encodes any of the soluble endoglin polypeptides of the invention. A non-limiting example of a nucleic acid that encodes a soluble endoglin polypeptide is shown in FIG. 1 (SEQ ID NO: 4). Desirably, the soluble endoglin nucleic acid encodes a soluble endoglin polypeptide containing a sequence that is at least 85% identical to SEQ ID NO: 2 that has a soluble endoglin biological activity. Non-limiting examples of soluble endoglin nucleic acids contain a sequence that is substantially identical (at least 85%, 90%, 95%, 96%, 97%, 98%, 99%, or 100% identical) to the nucleic acid sequence set forth in FIG. 1 (SEQ ID NO: 4) and contain a sequence that encodes a polypeptide sequence that has a soluble endoglin biological activity and contain a sequence that is at least 70% identical (e.g., at least 75%, 80%, 85%, 90%, 95%, or 99% identical) to SEQ ID NO: 1 or SEQ ID NO: 2.

By "soluble endoglin-mediated disorder" is a disorder where an increase in soluble endoglin levels or an increase in soluble endoglin biological activity has been detected or implicated in the pathogenesis or development of the disorder. For example, a subject having an soluble endoglin-mediated disorder may have an increase (e.g., at least a 5%, 6%, 7%, 8%, 9%, 10%, 15%, 20%, 25%, 30%, 40%, 50%, 60%, 70%, 80%, 90%, or even 100% increase) in the expression level (e.g., polypeptide or mRNA levels) of soluble endoglin or may have an increase (e.g., at least 5%, 10%, 15%, 20%, 25%, 30%, 40%, 50%, 60%, 70%, 80%, 90%, or even 100% increase) in a biological activity of a soluble endoglin polypeptide as described herein. Non-limiting examples of soluble endoglin-mediated disorders include pregnancy-related hypertensive disorders (e.g., pre-eclampsia, eclampsia, gestational hypertension, chronic hypertension, HELLP syndrome, and pregnancy with a smaller-for-gestational-age (SGA) infant), pulmonary hypertension, cancer (where the soluble endoglin levels are elevated), and malaria. Additional examples include Alzheimer's disease, cerebral arteriovenous malformations, and left ventricular dysfunction. In addition, patients with diabetes having retinopathy and/or a high probability of 10-year cardiovascular risk and patients with diabetes and hypertension who have three or more damaged target organs (e.g., heart, vessels, and kidney) are also included in some embodiments.

By "soluble endoglin-preventive disorder" is meant a disorder where a decrease in the soluble endoglin levels (protein or mRNA) or the soluble endoglin biological activity has been detected or implicated in the pathogenesis of the disorder or where specific factors, such as TGF-β family proteins or TGFβ family receptors or events (e.g. fibrosis, angiogenesis, immune activation) that can be inhibited or modulated by soluble endoglin, contribute to the disorder. Non-limiting examples include fibrotic disorders of internal organs and the scarring of skin where TGF-β is a significant contributor, disorders characterized by excessive angiogenesis (e.g. hemangiomas, pulmonary capillary hemagiomatosis) or abnormal growth of blood vessel such as cancer (e.g., cancer of the breast, prostate, colon, lung, head and neck, liver, kidney, renal system, and endometrium) and inflammatory and immune disorders (e.g. excessive TGF-β may be related to autoimmune diseases). In one non-limiting example, a subject having a soluble endoglin-preventive disorder may have a decrease (e.g., at least 5%, 6%, 7%, 8%, 9%, 10%, 15%, 20%, 25%, 30%, 40%, 50%, 60%, 70%, 80%, 90%, or even 100% decrease) in the expression level (e.g., polypeptide or mRNA levels) of soluble endoglin or may have a decrease (e.g., at least 5%, 6%, 7%, 8%, 9%, 10%, 15%, 20%, 25%, 30%, 40%, 50%, 60%, 70%, 80%, 90%, or even 100% decrease) in a biological activity of a soluble endoglin polypeptide as compared to a normal reference as described herein.

By "epitope" is meant a sequence of amino acids which, either as a result of linear structure or three dimensional conformation, forms the binding site for an antibody.

By "expression" is meant the detection of a gene or polypeptide by standard art known methods. For example, polypeptide expression is often detected by Western blotting, DNA expression is often detected by Southern blotting or polymerase chain reaction (PCR), and RNA expression is often detected by northern blotting, PCR, or RNAse protection assays. Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Exemplary assays are described in detail in U.S. Patent Application Publication No. 2006/0067937 and PCT Publication Nos. WO 06/034507, WO 07/030,283, and WO 08/030,283. Any compound that decreases the presently described soluble endoglin polypeptide or nucleic acid expression levels by at least 5% (e.g., at least 6%, 7%, 8%, 9%, 10%, 15%, 20%, 25%, 30%, 40%, 50%, 60%, 70%, 80%, 90%, or more) is desirable for methods of treating or decreasing the likelihood of developing a soluble endoglin-mediated disorder. Any compound that increases the presently described soluble endoglin polypeptide or nucleic acid expression levels by at least 5% (e.g., at least 6%, 7%, 8%, 9%, 10%, 15%, 20%, 25%, 30%, 40%, 50%, 60%, 70%, 80%, 90%, or more) is desirable for methods of treating or decreasing the likelihood of developing a soluble endoglin-preventive disorder.

By "fragment" is meant a portion of a polypeptide or nucleic acid molecule. This portion contains, preferably, at least 5%, 10%, 15%, 20%, 25%, 30%, 35%, 40%, 45%, 50%, 55%, 60%, 65%, 70%, 75%, 80%, 85%, or 90% of the entire length of the soluble endoglin nucleic acid molecule (e.g., a sequence that is at least 95% identical to SEQ ID NO: 4) or polypeptide of the invention (e.g., a sequence that is at least 95% identical to SEQ ID NO: 3). A fragment of a soluble endoglin nucleic acid of the invention may contain at least 10, 20, 30, 40, 50, 60, 70, 80, 90, 100, 150, 200, 250, 300, 350, 400, 450, 500, 550, 600, 700, 800, 900, 1000, 1100, 1200, 1300, 1332, or more nucleotides or at least 6, 7, 8, 9, 10, 20, 25, 30, 35, 40, 45, 50, 55, 60, 65, 70, 75, 80, 85, 90, 95, 100, 105, 110, 115, 120, 125, 130, 135, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, or 440 amino acids or more. The fragments of a soluble endoglin polypeptide have a soluble endoglin polypeptide activity and contain a sequence that is substantially identical (e.g., at least 70%, 71%, 72%, 73%, 74%, 75%, 80%, 81%, 82%, 83%, 84%, 85%, 90%, 95%, 96%, 97%, 98%, 99%, or 100% identical) to SEQ ID NO: 1 or SEQ ID NO: 2. The fragments of a nucleic acid encoding a soluble endoglin polypeptide desirably contain a nucleic acid sequence that encodes a polypeptide sequence that has a soluble endoglin biological activity and contains a sequence that is substantially identical (e.g., at least 70%, 71%, 72%, 73%, 74%, 75%, 80%, 81%, 82%, 83%, 84%, 85%, 90%, 95%, 96%, 97%, 98%, 99%, or 100% identical) to SEQ ID NO: 1 or SEQ ID NO: 2. Exemplary fragments of soluble endoglin polypeptide have a soluble endoglin biological activity and include a contiguous amino acid sequence from 1 to 444 amino acids (e.g., SEQ ID NO: 3) (including the peptide leader sequence) or a contiguous amino acid sequence from 1 to 418 amino acids (e.g., fragments excluding amino acids 1 to 25 of SEQ ID NO: 3, as shown in FIGS. 3A and 3B). Additional exemplary fragments have a soluble endoglin biological activity and contain a sequence identical to SEQ ID NO: 1 or SEQ ID NO: 2 at the C-terminus.

By "gestational hypertension" is meant the development of high blood pressure without proteinuria after 20 weeks of pregnancy.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

By "metastatic disease," "metastases," and "metastatic lesion" are meant a group of cells which have migrated to a site distant relative to the primary tumor. "Non-metastatic" refers to tumor cells, e.g., human cancer cells, that are unable to establish secondary tumor lesions distant to the primary tumor. Although not often the case, metastatic disease can occur when no primary tumor has been detected. The cells in a metastatic tumor resemble those in the primary tumor. Metastasis or metastatic disease can be diagnosed in a variety of ways that are known in the art.

By "nitric oxide synthase" or "NOS" is meant an enzyme that catalyzes the formation of nitric oxide (NO) from oxygen and arginine. NOS is a complex enzyme containing several cofactors, a heme group which is part of the catalytic site, an N-terminal oxygenase domain, which belongs to the class of heme-thiolate proteins, and a C-terminal reductase domain which is homologous to NADPH:P450 reductase. NOS produces NO by catalyzing a five-electron oxidation of a guanidino nitrogen of L-arginine (L-Arg). Oxidation of L-Arg to L-citrulline occurs via two successive monooxygenation reactions producing N-hydroxy-L-arginine as an intermediate. The interdomain linker between the oxygenase and reductase domains contains a calmodulin-binding sequence. NO functions at low concentrations as a signal in many diverse physiological processes such as blood pressure control, neurotransmission, learning and memory, and at high concentrations as a defensive cytotoxin.

In mammals, three distinct genes encode NOS isozymes: neuronal NOS (nNOS or NOS-1), cytokine-inducible NOS (iNOS or NOS-2), and endothelial NOS (eNOS or NOS-3). eNOS is membrane associated and its localization to endothelial membranes is mediated by cotranslational N-terminal myristoylation and post-translational palmitoylation. In preferred embodiments of the invention, the NOS is eNOS.

By "operably-linked" is meant that a gene and a regulatory sequence(s) are connected in such a way as to permit gene expression when the appropriate molecules (e.g., transcriptional activator proteins) are bound to the regulatory sequence(s).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, (20$^{th}$ edition), ed. A. Gennaro, 2000, Lippincott, Williams & Wilkins, Philadelphia, Pa. One or more of the soluble endoglin polypeptides or nucleic acids of the invention may be administered in a pharmaceutically acceptable carrier to a subject (e.g., a human).

By "pregnancy-related hypertensive disorder" is meant any condition or disease during pregnancy that is associated with or characterized by an increase in blood pressure. Included among these conditions are pre-eclampsia (including premature pre-eclampsia, severe pre-eclampsia), eclampsia, gestational hypertension, HELLP syndrome, (hemolysis, elevated liver enzymes, low platelets), abruption placenta, chronic hypertension, pregnancy with intrauterine growth restriction, and pregnancy with a small for gestational age (SGA) infant. It should be noted that although pregnancy with a SGA infant is not often associated with hypertension, it is included in this definition.

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. All forms of pre-eclampsia, such as premature, mild, moderate, and severe pre-eclampsia are included in this definition. Pre-eclampsia generally occurs after the 20$^{th}$ week of gestation. Pre-eclampsia is generally defined as some combination of the following symptoms: (1) a systolic blood pressure (BP)>140 mmHg and a diastolic BP>90 mmHg after 20 weeks gestation (generally measured on two occasions, 4-168 hours apart), (2) new onset proteinuria (1+ by dipstick on urinalysis, >300 mg of protein in a 24-hour urine collection, or a single random urine sample having a protein/creatinine ratio>0.3), and (3) resolution of hypertension and proteinuria by 12 weeks postpartum. Severe pre-eclampsia is generally defined as (1) a diastolic BP>110 mmHg (generally measured on two occasions, 4-168 hours apart) or (2) proteinuria characterized by a measurement of 3.5 grams or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. HELLP syndrome is characterized by evidence of thrombocytopenia (<100,000 cells/µl), increased LDH (>600 IU/L), and increased AST (>70 IU/L). Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage and periportal necrosis) and the central nervous system (e.g., cerebral edema and cerebral hemorrhage). The etiology of the seizures is thought to be secondary to the development of cerebral edema and focal spasm of small blood vessels in the kidney.

By "premature pre-eclampsia" is meant pre-eclampsia with onset of symptoms <37 weeks or <34 weeks.

By "prostacyclin" or "PGI$_2$" is meant a member of the family of lipid molecules known as eicosanoids. It is produced in endothelial cells from prostaglandin H2 (PGH2) by the action of the enzyme prostacyclin synthase and is mainly synthesized by the vascular endothelium and by smooth muscle. PGI$_2$ biological activity includes inhibition of platelet aggregation, relaxation of smooth muscle, reduction of systemic and pulmonary vascular resistance by direct vasodilation, and natriuresis in the kidney.

By "purified" or "isolated" is meant separated from other components that naturally accompany it. Typically, a compound (e.g., nucleic acid, polypeptide, or small molecule) is isolated when it is at least 50%, by weight, free from proteins, flanking nucleic acids, antibodies, and naturally-occurring organic molecules with which it is naturally associated. Preferably, the factor is at least 75%, more preferably, at least 80%, 85%, or 90%, and most preferably, at least 95% or 99%, by weight, isolated. An isolated factor may be obtained by chemical synthesis, separation of the factor from natural sources, or production of the factor in a recombinant host cell that does not naturally produce the factor. Proteins and small molecules may be purified by one skilled in the art using standard techniques such as those described by Ausubel et al. (Current Protocols in Molecular Biology, John Wiley & Sons, New York, 2000). The factor is preferably at least 2, 3, 4, 5, or 10 times as pure or isolated as the starting material, as measured using polyacrylamide gel electrophoresis, column chromatography, optical density, HPLC analysis, or Western blot analysis (Ausubel et al., supra). Preferred methods of purification include immunoprecipitation, column chromatography (such as immunoaffinity chromatography), magnetic bead immunoaffinity purification, and panning with a plate-bound antibody.

By "reduce or inhibit" is meant the ability to cause an overall decrease preferably of at least 5%, 6%, 7%, 8%, 9%, 10%, 15%, 20%, 25%, 30%, 35%, 40%, 45%, 50% or more, and more preferably an overall decrease of at least 60%, 70%, 75%, 80%, 85%, 90%, 95% or more. For example, in some embodiments of the invention, reduce or inhibit can refer to the levels (polypeptide or mRNA levels) or a biological activity of a soluble endoglin polypeptide of the invention, symptoms of the disorder being treated, the presence or size of metastases, the size of the primary tumor, or a biological activity of a TGF-β family member.

By "control" or "reference" is meant any sample, standard, or level that is used for comparison purposes. For diagnostic or therapeutic monitoring purposes, a control sample may be a prior sample taken from the same subject (e.g., a sample harvested at a prior time point or prior to the onset of symptoms). Non-limiting examples of control samples include: a sample from a pregnant subject or group of subjects not having a pregnancy related hypertensive disorder, such as pre-eclampsia or eclampsia; a subject or group of subjects that is pregnant but the sample was taken early in pregnancy (e.g., in the first or second trimester or before the detection of a pregnancy related hypertensive disorder, such as pre-eclampsia or eclampsia); a subject or group of subjects that is pregnant and has no history of a pregnancy-related hypertensive disorder, such as pre-eclampsia or eclampsia; a subject or group of subjects that is not pregnant; a sample from a subject or group of subjects not having a soluble endoglin-preventive disorder (e.g., cancer or a cardiovascular disorder); a sample of a purified reference polypeptide at a known normal concentration (i.e., not indicative of a soluble endoglin-mediated disorder, such as pre-eclampsia or eclampsia, or not indicative of a soluble endoglin-preventive disorder). Additional examples of control samples can be prepared from a subject or group of subjects prior to developing or diagnosis with a soluble endoglin-mediated disorder or a soluble endoglin-preventive disorder (e.g., prior to the onset of one or more symptoms of a soluble endoglin-mediated disorder or a soluble endoglin-preventive disorder). By "control standard or level" is meant a value or number derived from a control sample. For example, a control standard or level can be a value or number derived from a normal subject or group of subjects that is matched to the sample subject, for example, by at least one of the following criteria: age, sex, weight, gestational age of the fetus, maternal age, maternal blood pressure prior to pregnancy, maternal blood pressure during pregnancy, BMI of the mother, weight of the fetus, prior diagnosis of pre-eclampsia or eclampsia, and a family history of pre-eclampsia or eclampsia. A "positive control" sample, standard or value is a sample or value or number derived from a subject or group of subjects that is known to have a soluble endoglin-mediated disorder or a soluble endoglin-preventive disorder. For example, a positive control sample may be from a subject or group of subjects having a pregnancy-related hypertensive disorder (e.g., pre-eclampsia or eclampsia), that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of a pregnancy-related hypertensive disorder, and a family history of a pregnancy related hypertensive disorder. Additional positive controls may be from a subject of group of subjects having the same soluble endoglin-mediated disorder or soluble endoglin-preventive disorder that is matched for one or more criteria, such as sex, age, and weight.

By "sample" is meant a tissue biopsy, cell (e.g., endothelial cell or tumor cell), bodily fluid (e.g., blood, serum, plasma, urine, saliva, amniotic fluid, or cerebrospinal fluid) or other specimen obtained from a subject. Desirably, the biological sample includes soluble endoglin nucleic acids or polypeptides of the invention, or both.

By "small RNA" is meant an isolated RNA molecule, either single-stranded or double stranded that is at least 15 nucleotides, preferably, 17, 18, 19, 20, 21, 22, 23, 24, 25, 26, 27, 28, 29, 30, 31, 32, 33, 34, or 35 nucleotides in length and even up to 50 or 100 nucleotides in length (inclusive of all integers in between). Preferably, the small RNA is capable of mediating RNAi. As used herein the phrase "mediates RNAi" refers to (indicates) the ability to distinguish which RNAs are to be degraded by the RNAi machinery or process. Included within the term small RNA are "small interfering RNAs" and "microRNA." In general, microRNAs (miRNAs) are small (e.g., 17-26 nucleotides), single-stranded noncoding RNAs that are processed from approximately 70 nucleotide hairpin precursor RNAs by Dicer. Small interfering RNAs (siRNAs) are of similar size and are also non-coding, however, siRNAs are processed from long dsRNAs and are usually double-stranded (e.g., endogenous siRNAs). siRNAs can also include short hairpin RNAs in which both strands of an siRNA duplex are included within a single RNA molecule. Small RNAs can be used to describe both types of RNA. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution, and/or alteration of one or more nucleotides. Such alterations can include addition of non-nucleotide material, such as to the end(s) of the small RNA or internally (at one or more nucleotides of the RNA). Nucleotides in the RNA molecules of the present invention can also comprise non-standard nucleotides, including non-naturally occurring nucleotides or deoxyribonucleotides. Small RNAs of the present invention need only be sufficiently similar to natural RNA that it has the ability to mediate RNAi.

By "specifically binds" is meant a compound or antibody which recognizes and binds a soluble endoglin polypeptide or nucleic acid of the invention, but that does not substantially recognize and bind other molecules in present in a sample (e.g., a biological sample which naturally includes a soluble endoglin polypeptide or nucleic acid of the invention). In one example, an antibody that specifically binds a soluble endoglin polypeptide of the invention does not bind membrane-bound endoglin or other forms of soluble endoglin. Desirably, an antibody or antibody-binding fragment thereof specifically binds to an epitope containing a sequence that is at least 70% identical (e.g., at least 71%, 72%, 73%, 74%, 75%, 80%, 81%, 82%, 83%, 84%, 85%, 90%, 95%, 96%, 97%, 98%, 99%, or 100% identical) to the sequence of SEQ ID NO: 1 or SEQ ID NO: 2, or a fragment thereof (e.g., 3 amino acids, 4 amino acids, 5 amino acids, or 6 amino acids).

By "subject" is meant a mammal, including, but not limited to, a human or non-human mammal, such as a cow, a horse, a sheep, a pig, a goat, a dog, or a cat. Included in this definition are pregnant, post-partum, and non-pregnant mammals.

By "substantially identical" is meant a nucleic acid or amino acid sequence that, when optimally aligned, for example using the methods described below, share at least 70%, 71%, 72%, 73%, 74%, 75%, 80%, 81%, 82%, 83%, 84%, 85%, 90%, 95%, 96%, 97%, 98%, 99%, or even 100% sequence identity with a second nucleic acid or amino acid sequence, e.g., a soluble endoglin sequence such as SEQ ID NO: 1, SEQ ID NO: 2, SEQ ID NO: 3, or SEQ ID NO: 4. "Substantial identity" may be used to refer to various types and lengths of sequence, such as a full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman, *J. Mol. Biol.* 147:195-7, 1981); "BestFit" (Smith and Waterman, Advances in Applied Mathematics, 482-489, 1981) as incorporated into GeneMatcher Plus™; BLAST program (Basic Local Alignment Search Tool), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 6 amino acids, preferably at least 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, or 444 amino acids, or more. For nucleic acids, the length of comparison sequences will generally be at least 20, 25, 30, 50, 100, 125, 150, 200, 250, 300, 350, 400, 450, 500, 550, 600, 650, 700, 750, 800, 850, 900, 950, 1000, 1050, 1100, 1150, 1200, 1250, 1300, or 1330 nucleotides, or more. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "transforming growth factor β (TGF-β)" is meant a mammalian growth factor that has TGF-β biological activity and is a member of a family of structurally related paracrine polypeptides found ubiquitously in vertebrates, and prototypic of a large family of metazoan growth, differentiation, and morphogenesis factors (see, for review, Massaque et al. *Ann. Rev. Cell. Biol.* 6:597-641, 1990; Massaque et al. *Trends Cell. Biol.* 4:172-178, 1994; Kingsley *Gene Dev.* 8:133-146, 1994; and Sporn et al. *J. Cell. Biol.* 119:1017-1021, 1992. As described in Kingsley, supra, the TGF-β superfamily has at least 25 members, and can be grouped into distinct sub-families with highly related sequences. The most obvious sub-families include the following: the TGF-β subfamily, which comprises at least four genes that are much more similar to TGF-β1 than to other members of the TGF-β superfamily; the bone morphogenetic proteins; the activin sub-family, comprising homo- or hetero-dimers or two subunits, inhibinβ-A and inhibinβ-B. The decapentaplegic subfamily, which includes the mammalian factors BMP2 and BMP4, can induce the formation of ectopic bone and cartilage when implanted under the skin or into muscles. The 60A subfamily includes a number of mammalian homologs with osteoinductive activity, including BMP5-8. Other members of the TGF-β superfamily include the gross differentiation factor 1 (GDF-1), GDF-3/VGR-2, dorsalin, nodal, mullerian-inhibiting substance (MIS), and glial-derived neurotrophic growth factor (GDNF). It is noted that the DPP and 60A subfamilies are related more closely to one another than to other members of the TGF-β superfamily, and have often been grouped together as part of a larger collection of molecules called DVR (dpp- and vgl-related). Unless evidenced from the context in which it is used, the term TGF-β as used throughout this specification will be understood to generally refer to members of the TGF-β superfamily as appropriate (Massague et al., *Annu. Rev. Biochem.* 67:753-91, 1998; Josso et al., *Curr. Op. Gen. Dev.*, 7:371-377, 1997). TGF-β functions to regulate growth, differentiation, motility, tissue remodeling, neurogenesis, wound repair, apoptosis, and angiogenesis in many cell types. TGF-β also inhibits cell proliferation in many cell types and can stimulate the synthesis of matrix proteins.

By "therapeutic amount" is meant an amount that when administered, either by direct administration or by an ex vivo approach, to a patient suffering from a soluble endoglin-preventive disorder or a soluble endoglin-mediated disorder is sufficient to cause a qualitative or quantitative reduction (e.g., at least a 5%, 10%, 15%, 20%, 25%, 30%, 35%, 40%, 45%, 50%, 60%, 70%, 80%, 90%, or even 100% reduction) in one or more (e.g., 2, 3, 4, 5, or 6) of the symptoms of the soluble endoglin-preventive disorder or the soluble endoglin-mediated disorder (described below). A therapeutic amount may also mean an amount that when administered results in a decrease (e.g., at least a 5%, 10%, 15%, 20%, 25%, 30%, 35%, 40%, 45%, 50%, 60%, 70%, 80%, 90%, or even 100% reduction) in the likelihood of developing a soluble endoglin-preventive disorder or a soluble endoglin-mediated disorder.

By "treating" or "ameliorating" is meant treating or ameliorating a condition or symptom(s) of the condition (e.g., the symptoms of soluble endoglin-preventive disorders or the symptoms of soluble endoglin-mediated disorders described herein). To "treat disease" or use for "therapeutic treatment" refers to administering the treatment to a subject already suffering from a disease to improve the subject's condition. Preferably, the subject is diagnosed with or identified as having a predisposition for developing a soluble endoglin-mediated disorder or a soluble endoglin-preventive disorder. As compared with an equivalent untreated control, such amelioration or degree of treatment is at least 5%, 10%, 20%, 30%, 40%, 50%, 60%, 70%, 80%, 90%, 95%, 99%, or 100%, as measured by any standard technique.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably-linked to a gene or coding region such that, upon transfection into a recipient cell, an RNA or an encoded protein or is expressed.

BRIEF DESCRIPTION OF THE DRAWINGS

FIG. 1 provides the nucleic acid (SEQ ID NO: 4) and amino acid sequence of full length human soluble endoglin (HsEng) (SEQ ID NO: 3).

FIG. 2A is a schematic diagram that shows the human endoglin mRNA comprised of 14 exons and the alternatively spliced human Eng-mRNA transcript, which contains a unique 3' sequence and UTR. The HsEng mRNA transcript is generated by exon extension whereby exon 9b is "extended" by 372 bases into intron 10. cDNA sequencing revealed that this novel 1683-base Eng mRNA transcript is comprised of the same translation start site as the full-length form of Eng but harbors a stop codon at position 1333 and 351 bp of untranslated region (UTR). The underlined portion indicates the C-terminal amino acid sequence of HsEng (SEQ ID NO: 2). FIG. 2B is a graph showing the expression of the HsEng transcript in human tissues relative to 18S RNA levels using Taqman primer/probe sets. HsEng transcript is enriched in human lung, placenta, uterus and testes.

FIGS. 3A and 3B are schematic diagrams showing the organization of the orphan and zona pellucida (ZP) domains, as well as the transmembrane/cytoplasmic region of endoglin expressed on the plasma membrane of cells. The signal peptide consisting of the first 25 amino acids is cleaved upon expression of the protein on surface of cells. A putative proteolytic cleavage site has been suggested at Arg437 within the ZP domain. HsEng protein consists of 444-amino acid and harbors a unique peptide, -VRWTVTC-, as a result of alternative pre-mRNA splicing. The same signal peptide (Met1-Ala25) is cleaved and is necessary for its expression. FIG. 3C is a representative IP-western blot showing the expression of soluble endoglin protein with an apparent molecular weight of ~64 kD under both non-reducing and reducing conditions in the cultured media taken after overexpression of soluble endoglin cDNA in bovine aortic endothelial cells. While a relatively small portion of sEng was also detected as a ~125 kD dimer, it exists predominantly as a monomer. FIG. 3D is a representative IP-western blot showing the detection of soluble endoglin (HsEng) using an antibody (C-5144) to the novel carboxy terminal sequence unique to soluble endoglin. An increase in soluble endoglin was specifically detected in the sera of patients with pre-eclampsia (PE) vs. normal controls (C).

FIGS. 9A-9B show representative graphs and a blot showing HsEng mRNA levels (9A) and HsEng protein levels (9B) in the condition media after treatment of HMVEC-L with TNF-α.

DETAILED DESCRIPTION

Figure 4:
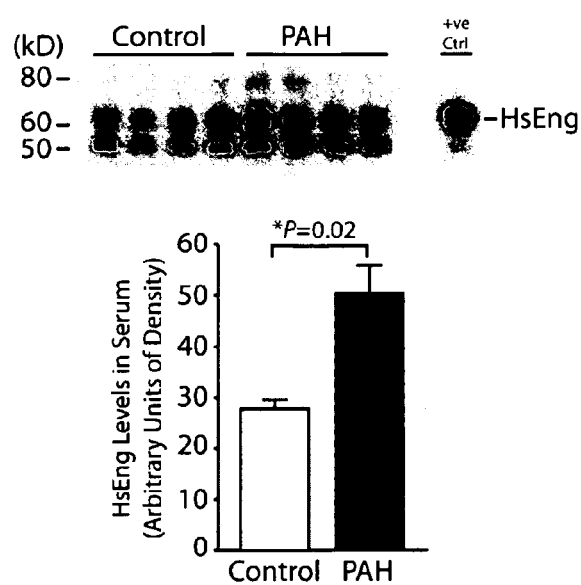
FIG. 4 shows a representative IP-Western blot showing significantly elevated HsEng levels in sera of patients with PAH. HsEng detected in these serum samples had the same apparent molecular weight (~64 kD) as the positive control, consisting of the conditioned medium of HEK293T cells transfected with HsEng cDNA.

We have discovered a form of soluble endoglin produced by alternative splicing of the endoglin precursor mRNA. We have isolated this previously unrecognized mRNA transcript of endoglin from human tissue and discovered that it encodes a stable and soluble (secreted) protein. This soluble form of endoglin exists predominantly as a monomer and is able to modulate TGF-β/BMP signaling. The soluble endoglin described herein includes a unique C-terminal amino acid sequence of amino acids 437-444 of RVRWTVTC (SEQ ID NO: 1) or amino acids 438-444 of VRWTVTC (SEQ ID NO: 2) and has a soluble endoglin biological activity. The unique C-terminal amino acid sequences and the complete amino acid and nucleic acid sequences of the alternatively spliced mRNA transcript of soluble endoglin are shown in FIGS. 2A, 3B, and 1, respectively.

Soluble Endoglin Polypeptides

The invention features isolated forms of soluble endoglin polypeptides or fragments thereof desirably greater than 10 amino acids in length (e.g., at least 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, or 440 amino acids or more), having a soluble endoglin biological activity, and containing a sequence that has at least 70% sequence identity (e.g., at least 71%, 72%, 73%, 74%, 75%, 80%, 81%, 82%, 83%, 84%, 85%, 90%, 95%, 96%, 97%, 98%, 99%, or 100% identical) to RVRWTVTC (SEQ ID NO: 1) or VRWTVTC (SEQ ID NO: 2) (see, FIGS. 1, 2A, and 3A-B). A soluble endoglin polypeptide may contain at least 444 amino acids and have a soluble endoglin biological activity. Desirably, the soluble endoglin polypeptide has a soluble endoglin biological activity and includes a sequence that is at least 85% identical (e.g., at least 90%, 91%, 92%, 93%, 94%, 95%, 96%, 97%, 98%, 99%, or even 100% identical) to SEQ ID NO: 3 (FIG. 1) (when an equal number of amino acids in the soluble endoglin polypeptide are compared to the same number of amino acids in SEQ ID NO: 3) or a sequence that is at least 70% identical (e.g., at least 71%, 72%, 73%, 74%, 75%, 80%, 81%, 82%, 83%, 84%, 85%, 90%, 95%, 96%, 97%, 98%, 99%, or 100% identical) to SEQ ID NO: 2. In one non-limiting example, the isolated soluble endoglin polypeptide has a soluble endoglin biological activity and includes or consists of the amino acid sequence of SEQ ID NO: 3. In another example, a soluble endoglin polypeptide has a soluble endoglin biological activity and contains a sequence that is at least 70%, desirably at least 95%, 96%, 97%, 98%, 99%, or 100% identical, to SEQ ID NO: 1 or SEQ ID NO: 2 at the C-terminus.

The invention also provides fragments of the above described soluble endoglin polypeptides that have a soluble endoglin biological activity. These fragments may exclude the signal sequence encoded by amino acids 1-26 of SEQ ID NO: 3 (see FIG. 1). Fragments of the soluble endoglin polypeptide have a soluble endoglin biological activity, contain at least 10 contiguous amino acids (e.g., at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, or 440 amino acids or more), and contain a sequence that has at least 70% sequence identity (e.g., at least 71%, 72%, 73%, 74%, 75%, 80%, 81%, 82%, 83%, 84%, 85%, 90%, 95%, 96%, 97%, 98%, 99%, or 100% identical) to SEQ ID NO: 2.

The provided soluble endoglin polypeptides and fragments may also contain additional N- and/or C-terminal sequences. For example, additional N- and/or C-terminal sequences may be added to a soluble endoglin polypeptide, having a soluble endoglin biological activity and containing a sequence is at least 85% identical (e.g., at least 90%, 91%, 92%, 93%, 94%, 95%, 96%, 97%, 98%, 99%, or even 100% identity) to SEQ ID NO: 3, or a fragment thereof, that has a soluble endoglin biological activity. The additional N- and/or C-terminal sequences may be at least 5 contiguous amino acids (e.g., at least 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 250, 300, 350, 400, 450, 500, 550, or 600 amino acids). Examples of additional N- and/or C terminal sequences that may be covalently attached to a soluble endoglin polypeptide or fragment are described below.

The soluble endoglin polypeptides or fragments provided have a soluble endoglin biological activity, e.g., one or more biological activity selected from, but not limited to: the ability to bind to TGF-β1, the ability to bind to TGF-β2, the ability to bind to activin-A, the ability to bind to BMP-2, the ability to bind to BMP-7 or BMP-9, the ability to bind TGF-β receptor I, the ability to bind to TGF-β receptor II, the ability to bind BMP receptor II, the ability to reverse or inhibit angiogenesis, the ability to reduce or inhibit Smad 2/3-dependent transcriptional activation, and the ability to inhibit eNOS activation. The soluble endoglin polypeptides or fragments desirably act as antagonists of endoglin or endoglin signaling pathways, to create a deficiency of TGF-β and other known ligands by acting as a physiological sink to bind ligands, and decrease TGF-β signaling in cells (e.g., an endothelial cell).

Soluble endoglin polypeptides useful in the methods of the invention include any soluble endoglin polypeptide having a soluble endoglin biological activity, containing a sequence that is at least 70% identical (e.g., at least 71%, 72%, 73%, 74%, 75%, 80%, 81%, 82%, 83%, 84%, 85%, 90%, 95%, 96%, 97%, 98%, 99%, or 100% identical) to the sequence of SEQ ID NO: 2, or any homologs, fragments, derivatives, or analogs thereof that have a soluble endoglin biological activity.

Soluble endoglin polypeptides, fragments, derivatives, and analogs of the invention can be produced by any of a variety of methods for protein production known in the art, such as purification of naturally occurring soluble endoglin polypeptides (e.g., from the placenta), products of chemical synthetic procedures, and products produced by recombinant techniques from a prokaryotic or eukaryotic host, including, for example, bacterial, fungus, higher plant, insect, and mammalian cells. In one example, a soluble endoglin polypeptide of the invention is produced by recombinant DNA methods by inserting a DNA sequence encoding a soluble endoglin polypeptide, or a fragment, derivative, or analog thereof, into a recombinant expression vector and expressing the DNA sequence under conditions promoting expression. General techniques for nucleic acid manipulation are described, for example, by Sambrook et al., in "Molecular Cloning: A Laboratory Manual," 2nd Edition, Cold Spring Harbor Laboratory press, 1989; Goeddel et al., in "Gene Expression Technology Methods in Enzymology," Academic Press, San Diego, Calif., 1990; Ausubel et al., in "Current Protocols in Molecular Biology," John Wiley & Sons, New York, N.Y., 1998; Watson et al., "Recombinant DNA," Chapter 12, 2nd edition, Scientific American Books, 1992; and other laboratory textbooks. The DNA encoding soluble endoglin polypeptide or a fragment, derivative, or analog of the invention can be operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites and sequences, which control the termination of transcription and translation. The ability to replicate in a host, usually conferred by an origin of replication, and a selection gene to facilitate recognition of transformants may additionally be incorporated.

Appropriate cloning and expression vectors for use with bacterial, fungal, yeast, and mammalian cellular hosts can be found, for example, in "Cloning Vectors: A Laboratory Manual," Elsevier, New York, 1985.

The expression construct is introduced into the host cell using a method appropriate to the host cell, as will be apparent to one of skill in the art. The expression construct can be introduced for transient expression of the protein or stable expression by selecting cells using a selectable marker in order to generate a stable cell line that expresses the protein continuously. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells for expression of soluble endoglin polypeptide of the invention from recombinant vectors include prokaryotes, and fungal, mammalian, or insect cells.

In one embodiment, for recombinant expression of the full-length soluble endoglin, a nucleic acid encoding amino acids 1-444 (as shown in FIG. 1) are included in the construct used for expression and purification of the protein. In another embodiment, the soluble endoglin undergoes post-translation modification, including but not limited to glycosylation and s-nitrosylation and oxidation of a cysteine residue during expression and purification. S-nitroslyation of soluble endoglin prevents its dimerization and may modulate its biological activity.

In addition, soluble endoglin polypeptides, fragments, derivatives, or analogs of the invention may be expressed in transgenic mammals (e.g., mice and bovines) such that the soluble endoglin is released into the milk of the transgenic animals. For example, the pBC1 Milk Expression Vector Kit (Genzyme Transgenics Corporation and Invitrogen Corporation) provides a milk expression vector which features a casein expression promoter upstream of restriction site sequences (for insertion of the expressed transgene). Methods of making transgenic animals and the purification of transgenically-expressed soluble proteins from the milk of such animals are known in the art.

Purified soluble endoglin polypeptide, or biologically active fragments, derivatives, or analogs of the invention, are prepared by culturing suitable host/vector systems to express the recombinant proteins. As a secreted protein, soluble endoglin polypeptide is likely to be released and can then be purified from culture media or cell extracts.

In one example, supernatants from systems which secrete recombinant protein into culture media can be first concentrated using a commercially available protein concentration filter, for example, an Amicon or Millipore Pellicon ultrafiltration unit, and then purified.

In addition to the methods employing recombinant DNA, soluble endoglin polypeptides or fragments of the invention can be purified from sources that naturally produce this form of the protein. Examples of these sources include any mammalian tissue or cells, such as placental tissues. The soluble endoglin polypeptide from these sources can be purified and concentrated using any of the methods known in the art or described herein.

After purification, soluble endoglin polypeptide or fragment of the invention may be exchanged into different buffers and/or concentrated by any of a variety of methods known in the art, including, but not limited to, filtration and dialysis. The purified soluble endoglin polypeptide or fragment is preferably at least 80% or 85% pure, more preferably at least 90% or 95% pure, and most preferably at least 98% pure. Regardless of the exact numerical value of the purity, the soluble endoglin polypeptide is preferably sufficiently pure for use as a pharmaceutical product.

Soluble endoglin polypeptides, or fragments, derivatives, or analogs of the invention, can also be produced by chemical synthesis (e.g., by the methods described in "Solid Phase Peptide Synthesis," 2nd ed., The Pierce Chemical Co., Rockford, Ill., 1984). Modifications to the protein, such as those described below, can also be produced by chemical synthesis.

Modifications to Soluble Endoglin Polypeptides

The invention encompasses soluble endoglin polypeptides, or fragments, derivatives, or analogs having a soluble endoglin biological activity, which are modified during or after synthesis or translation.

Modifications to the sequence of a soluble endoglin polypeptide of the invention (e.g., polypeptides containing the sequence of SEQ ID NO: 1, SEQ ID NO: 2, or SEQ ID NO: 3) may be made by deletion, addition, or alteration of the amino acids incorporated into the soluble endoglin polypeptide during translation without destroying the activity of the protein. Such sequence modifications can be made to improve expression, stability, solubility, cellular uptake, or biological activity of the protein in the various expression systems. In one example, the post-translational modification is the S-nitrosylation of a cysteine in the soluble endoglin protein. For example, a mutation can increase or decrease the binding of soluble endoglin polypeptide to TGF-β (one soluble endoglin biological activity). Generally, substitutions are made conservatively and take into consideration the effect on one or more soluble endoglin biological activity. Mutations, deletions, or additions in nucleotide sequences constructed for expression of derivative or analog proteins or fragments thereof must, of course, preserve the reading frame of the coding sequences and preferably will not create complementary regions that could hybridize to produce secondary mRNA structures such as loops or hairpins which would adversely affect translation of the mRNA.

Post-translational modifications may provide additional advantages such as increased affinity; decreased off-rate; increased solubility, stability, and in vivo or in vitro circulating time of the polypeptide; or decreased immunogenicity; and include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, S-nitrosylation, disulfide bond formation, demethylation, formation of cysteine, formation of sulfonic, sulfenic, or sulfinic acid, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, for example, Creighton, "Proteins: Structures and Molecular Properties," 2nd Ed., W. H. Freeman and Co., N.Y., 1992; "Postranslational Covalent Modification of Proteins," Johnson, ed., Academic Press, New York, 1983; Seifter et al., *Meth. Enzymol.*, 182:626-646, 1990; Rattan et al., *Ann. N.Y. Acad. Sci.*, 663:48-62, 1992). Additionally, the soluble endoglin polypeptide of the invention may contain one or more non-classical amino acids. Non-classical amino acids include, but are not limited to, to the D-isomers of the common amino acids, 2,4-diaminobutyric acid, α-aminoisobutyric acid, 4-aminobutyric acid, Abu, 2-amino-butyric acid, g-Abu, e-Ahx, 6-amino-hexanoic acid, Aib, 2-aminoisobutyric acid, 3-amino-propionic acid, ornithine, norleucine, norvaline, hydroxyproline, sarcosine, citrulline, homocitrulline, cysteic acid, t-butylglycine, t-butylalanine, phenylglycine, cyclohexylalanine, α-alanine, fluoro-amino acids, designer amino acids such as α-methyl amino acids, Ca-methyl amino acids, Na-methyl amino acids, and amino acid analogs in general. Furthermore, the amino acid can be D (dextrorotary) or L (levorotary).

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression.

In one preferred example, the post-translational modification is S-nitrosylation of a cysteine in the soluble endoglin protein.

As described above, the invention also includes chemically-modified derivatives of the presently described soluble endoglin polypeptides, which may provide additional advantages such as increased solubility, stability, and circulating time of the polypeptide, or decreased immunogenicity (see, e.g., U.S. Pat. No. 4,179,337; incorporated by reference). The chemical moieties for derivitization may be selected from water soluble polymers such as, for example, polyethylene glycol, ethylene glycol/propylene glycol copolymers, carboxymethylcellulose, dextran, polyvinyl alcohol, and the like. The soluble endoglin polypeptide or fragment of the invention may be modified at random positions within the molecule, or at predetermined positions within the molecule and may include one, two, or three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). As noted above, the polyethylene glycol may have a branched structure. Branched polyethylene glycols are described, for example, in U.S. Pat. No. 5,643,575 (incorporated by reference); Morpurgo et al., *Appl. Biochem. Biotechnol.* 56:59-72, 1996; Vorobjev et al., *Nucleosides Nucleotides* 18:2745-2750, 1999; and Caliceti et al., *Bioconjug. Chem.* 10:638-646, 1999, the disclosures of each of which are incorporated by reference.

The polyethylene glycol molecules (or other chemical moieties) should be attached to the soluble endoglin polypeptide or fragment of the invention with consideration of effects on functional or antigenic domains of the protein. There are a number of attachment methods available to those skilled in the art, e.g., EP 0401384 (coupling PEG to G-CSF; herein incorporated by reference), see also Malik et al., *Exp. Hematol.* 20:1028-1035, 1992 (reporting pegylation of GM-CSF using tresyl chloride). For example, polyethylene glycol may be covalently bound through amino acid residues via a reactive group, such as a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or a lysine residue. The number of polyethylene glycol moieties attached to each polypeptide or fragment of the invention (i.e., the degree of substitution) may also vary. For example, the pegylated soluble endoglin polypeptide or fragment may be linked, on average, to 1, 2, 3, 4, 5, 6, 7, 8, 9, 10, 12, 15, 17, 20 or more polyethylene glycol molecules. Similarly, the average degree of substitution may vary within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per polypeptide or fragment molecule. Methods for determining the degree of substitution are discussed, for example, in Delgado et al., *Crit. Rev. Ther. Drug Carrier Sys.*, 9:249-304, 1992.

The soluble endoglin polypeptides of fragments of the invention may also be modified with a detectable label, including, but not limited to, an enzyme, prosthetic group, fluorescent material, luminescent material, bioluminescent material, radioactive material, positron emitting metal, non-radioactive paramagnetic metal ion, and affinity label for detection and isolation of a soluble endoglin target. The detectable substance may be coupled or conjugated either directly to the polypeptides of the invention or indirectly, through an intermediate (such as, for example, a linker known in the art) using techniques known in the art. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the soluble endoglin polypeptide of fragment of the invention or indirectly, through an intermediate (such as, for example, a linker known in the art) using techniques known in the art. See, for example, U.S. Pat. No. 4,741,900 (incorporated by reference) for metal ions, which can be conjugated to one of the provided soluble endoglin polypeptides or fragments for use in diagnostics according to the present invention.

The soluble endoglin polypeptide or fragment of the invention can also be modified by conjugation to another protein or therapeutic compound. Such conjugation can be used, for example, to enhance the stability or solubility of the protein, to reduce the antigenicity, or to enhance the therapeutic effects of the protein. A preferred fusion protein comprises a heterologous region from immunoglobulin (e.g., all or part of the Fc region) that is useful to solubilize proteins (see, EP-A 0232 262).

A soluble endoglin polypeptide or fragment of the invention may be conjugated to a therapeutic moiety such as a cytotoxin, e.g., a cytostatic or cytocidal agent, a chemotherapeutic agent, a radiotherapeutic agent, or a radioactive metal ion, e.g., alpha-emitters such as, for example, $^{213}$Bi or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof.

Additional therapeutic agents include, but are not limited to, antimetabolites (e.g., methotrexate, 6-mercaptopurine, 6-thioguanine, cytarabine, and 5-fluorouracil decarbazine), alkylating agents (e.g., mechlorethamine, thiotepa, chlorambuil, melphalan, carmustine (BSNU), lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label soluble endoglin polypeptides or fragments of the invention. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the relevant disclosures of each of which are hereby incorporated by reference in its entirety) and direct coupling reactions (e.g., Bolton-Hunter and Chloramine-T reaction).

Expression and Activity Assays for Soluble Endoglin Polypeptides

The expression levels of soluble endoglin (e.g., protein or mRNA) and the activity of the soluble endoglin polypeptides, fragments, derivatives, or analogs described herein may be measured using known methods (see, e.g., WO 07/143,023 and WO 08/030,283, incorporated by reference).

The following methods may be used to evaluate the biological activity of a soluble endoglin polypeptide, fragment, derivative, or analog of the invention and may also be used to determine ability of the compounds of the invention to decrease or increase soluble endoglin expression (e.g., protein or mRNA) or a soluble endoglin polypeptide biological activity in a subject.

To measure the ability of a compound to alter soluble endoglin polypeptide expression in a subject, blood serum from a subject may be measured for levels of soluble endoglin polypeptide of the invention, using methods such as ELISA, western blotting, or immunoassays using specific antibodies. Blood serum from the subject can also be measured for levels of TGF-β1, TGF-β3, activin-A, BMP2, BMP7, or any protein ligand known to bind to soluble endoglin polypeptide. Methods used to measure serum levels of these additional proteins include ELISA, western blotting, or immunoassays using specific antibodies. In addition, in vitro angiogenesis assays can be used to determine if the subject's blood has converted from an anti-angiogenic state to a pro-angiogenic state. Blood, serum, or urine samples from the subject can also be measured for levels of nucleic acids or polypeptides encoding eNOS, TGF-β1, TGF-β3, activin-A, BMP2, BMP7, or a soluble endoglin polypeptide of the invention. There are several art-known methods to assay for gene expression. Some examples include the preparation of RNA from the blood samples of the subject and the use of the RNA for northern blotting, PCR-based amplification, or RNAse protection assays. A decrease in the level of one of more of TGF-β1, TGF-β3, activin-A, BMP2, and BMP7 indicates that an administered soluble endoglin polypeptide, fragment, derivative, or analog of the invention has a soluble endoglin polypeptide biological activity or an administered compound has the effect of increasing soluble endoglin polypeptide biological activity or expression levels. Conversely, an increase in the level of one of more of TGF-β1, TGF-β3, activin-A, BMP2, and BMP7 indicates a decrease in soluble endoglin polypeptide biological activity or expression levels. In addition, the above methods for the measurement of the expression of a soluble endoglin (e.g., polypeptide or nucleic acid) can also be performed to measure the expression of a soluble endoglin of the invention in a cell (e.g., a cell cultured in vitro).

The ability of a soluble endoglin polypeptide, fragment, derivative, or analog of the invention to inhibit angiogenesis may be determined using the assays described in U.S. Patent Application Publication No. 2006/0067937 and PCT Publication No. WO 06/034507 (each incorporated by reference). In these experiments, Evans blue avidly binds to albumin and is used to quantify in vivo permeability in animals and humans (Green et al., J. Lab. Clin. Med. 111:173-183, 1988). Briefly, Balb-C mice are injected through the retro-orbital venous plexus with 1×10$^8$ pfu of adenovirus expressing GFP or soluble endoglin polypeptide and a microvascular permeability assay is performed 48 hours later. Mice are anesthetized by IP injection of 0.5 mL Avertin. 100 mL of 1% Evans blue dye (in PBS) is injected into the tail vein. 40 minutes later, mice are perfused via heart puncture with PBS containing 2 mM EDTA for 20 minutes. Organs (brain, lung, liver, and kidney) are harvested and incubated in formamide for 3 days to elute Evans blue dye. The optical density of the formamide solution is measured using 620 nm wavelength.

The ability of a soluble endoglin polypeptide, fragment, derivative, or analog of the invention to decrease microvascular reactivity may be determined using miscrovascular reactivity experiments as described in Maynard et al, J. Clin. Invest. 111:649-658, 2003 using rat renal microvessels (70-170 μm internal diameter). In these experiments, the relaxation properties of kidney microvessels are examined after pre-contraction of the microvessels with U46619 (thromboxane agonist) to 40-60% of their baseline diameter at a distending pressure of 40 mmHg Once the steady-state tone was reached, the responses to various reagents such as TGF-β1 or TGF-β3 or VEGF may be examined in a standardized order. In these assays, all drugs are applied extraluminally.

The ability of a soluble endoglin polypeptide, fragment, derivative, or analog of the invention to inhibit eNOS activation are described in WO 08/030,283 (incorporated by reference). The ability of a soluble endoglin polypeptide, fragment, derivative, or analog to bind a TGF-β family member (e.g., TGF-β1, TGF-β3, activin-A, and BMP), to bind a TGF-β receptor (e.g., TβRI and TβRII), to block binding of TGF-β1 to TβRII, and to inhibit TGF-β signaling pathways are known in the art and are described in WO 08/030,283 (incorporated by reference). Additional assays for soluble endoglin biological activity include reporter gene assays for downstream signaling proteins, such as Smad2/3-dependent transcription. Binding assays are also well known in the art. For example, a BIAcore instrument can be used to determine the binding constant of a complex between two proteins. The dissociation constant for the complex can be determined by monitoring changes in the refractive index with respect to time as buffer is passed over the chip (O'Shannessy et al., Anal. Biochem. 212:457-468, 1993; Schuster et al., Nature 365:343-347, 1993). Other suitable assays for measuring the binding of one protein to another include, for example, immunoassays such as enzyme-linked immunoabsorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Additional examples of such assays are known in the art.

Therapeutic Applications

The present invention features methods and compositions for treating or decreasing the likelihood of developing a soluble endoglin-mediated disorder or a soluble endoglin-preventive disorder (as described herein).

Soluble Endoglin-Mediated Disorders

The invention provides compositions and methods for treating or reducing the likelihood of developing a soluble endoglin-mediated disorder in a subject (e.g., a human). A soluble endoglin-mediated disorder is any disorder where increased soluble endoglin polypeptide or an increase in a soluble endoglin polypeptide biological activity is implicated in the pathogenesis or development of the disorder. Non-limiting examples of soluble endoglin-mediated disorders include pregnancy-related hypertensive disorders (e.g., preeclampsia, eclampsia, gestational hypertension, abruption placenta, pregnancy with intrauterine growth restriction, chronic hypertension, HELLP syndrome, pregnancy with a smaller-for-gestational age (SGA) infant), pulmonary hypertension, cancer (where soluble endoglin levels are increased) and malaria. Additional examples include Alzheimer's disease, cerebral arteriovenous malformations, and left ventricular dysfunction. In addition, patients with diabetes having retinopathy and/or a high probability of 10-year cardiovascular risk and patients with diabetes and hypertension who have three or more damaged target organs (e.g., heart, vessels, and kidney) are also included in some embodiments Compositions for treating, ameliorating, preventing, or reducing the likelihood of developing a soluble endoglin-mediated disorder preferably contain a compound that can decrease the expression levels (polypeptide, small molecule, or mRNA) or a biological activity of a soluble endoglin polypeptide (as described herein). Preferably, the compound is a purified antibody or antibody-binding fragment that specifically binds to the soluble endoglin polypeptide (e.g., specifically binds to an epitope containing a sequence that is at least 70%, 71%, 72%, 73%, 74%, 75%, 80%, 81%, 82%, 83%, 84%, 85%, 90%, 95%, 96%, 97%, 98%, 99%, or 100% identical to SEQ ID NO: 2, or a fragment thereof). The compound may also be an antisense nucleobase oligomer, an inhibitory nucleic acid (e.g., a dsRNA used to mediate RNA interference or a microRNA), or a small molecule (e.g., a compound capable of decreasing the expression level (polypeptide or mRNA) or a biological activity of a soluble endoglin polypeptide of the invention). Exemplary antisense nucleobase oligomers, antibodies, and compounds useful for the treatment of a soluble endoglin-mediated disorder are described below.

Antibodies, or antibody-binding fragments, thereof that specifically bind to soluble endoglin polypeptides or fragments described herein may be used to treat or prevent the development of a soluble endoglin-mediated disorder in a subject. Desirably, antibodies, or antibody-binding fragments thereof, specifically bind to an epitope that contains a sequence at least 70% identical (e.g., at least 71%, 72%, 73%, 74%, 75%, 80%, 81%, 82%, 83%, 84%, 85%, 90%, 95%, 96%, 97%, 98%, 99%, or 100% identical) to SEQ ID NO: 2, or a fragment thereof (e.g., 3 amino acids, 4 amino acids, 5 amino acids, or 6 amino acids). In one example, the antibody competes with C-5144 antibody for binding to soluble endoglin. The antibodies or antibody-binding fragments described herein may act as an antagonist or an agonist of a soluble endoglin polypeptide or fragment of the invention or may act as an antagonist or an agonist of a receptor that binds a soluble endoglin polypeptide or fragment of the invention. These antibodies and antibody fragments can be used to neutralize the activity of the soluble endoglin polypeptide or fragment blocking the binding of TGF-β1, TGF-β1, activin-A, BMP2, or BMP7. Soluble endoglin can also associate with its cell surface counterpart and can interact with the same receptors that the cell surface form of Eng is able to bind to and/or regulate including but not limited to receptors such as Alk-1, Alk-5, BMPR2. It is also possible that soluble endoglin may cause autonomous inhibition or activation of these receptors, independently of any ligand. Antibodies directed to the soluble endoglin of the invention can be used to neutralize any of the above activities of soluble endoglin.

Methods for the preparation and use of antibodies or antibody-binding fragments thereof for therapeutic purposes are described in several patents including U.S. Pat. Nos. 6,054,297; 5,821,337; 6,365,157; and 6,165,464; U.S. Patent Application Publication No. 2006/0067937; and PCT Publication No. WO 06/034507 (each incorporated by reference). Antibodies can be polyclonal, monoclonal, chimeric, bispecific, or a Fab fragment; monoclonal humanized antibodies are preferred.

The antibodies may be administered to the subject in a therapeutically effective amount. Preferably, the antibodies are administered parenterally or intravenously by continuous infusion. The dose and dosage regimen depends upon the severity of the soluble endoglin-mediated disorder, and the overall health of the subject. The amount of the antibody administered is typically in the range of about 0.001 to about 10 mg/kg of subject weight, preferably 0.01 to about 5 mg/kg of subject weight.

For parenteral administration, the antibodies are formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin Nonaqueous vehicles such as fixed oils and ethyl oleate may also be used. Liposomes may also be used as carriers. The vehicle may contain minor amounts of additives such as substances that enhance the isotonicity and chemical stability, e.g., buffers and preservatives. The antibodies are typically formulated in such vehicles at concentrations of about 1 mg/mL to 10 mg/mL.

Antisense nucleobase oligomers that reduce or inhibit the expression of a nucleic acid encoding a soluble endoglin polypeptide or fragment as described herein may be used to treat or prevent the development of a soluble endoglin-mediated disorder in a subject. By binding to the complementary nucleic acid sequence (e.g., a sequence that is at least 70%, 75%, 80%, 85%, 90%, 95%, or 100% identical to a sequence encoding SEQ ID NO: 2) (the sense or coding strand), antisense nucleobase oligomers are able to inhibit protein expression presumably through the enzymatic cleavage of the RNA strand by RNAse H. Preferably the antisense nucleobase oligomer is capable of reducing soluble endoglin polypeptide expression in a cell that expresses increased levels of soluble endoglin polypeptide as described herein. Preferably the decrease in the soluble endoglin polypeptide expression is at least 10% relative to cells treated with a control oligonucleotide, preferably 20% or greater, more preferably 40%, 50%, 60%, 70%, 80%, 90%, or greater. Methods for selecting and preparing antisense nucleobase oligomers are well known in the art. Methods for assaying levels of protein expression are also well known in the art and include western blotting, immunoprecipitation, and ELISA.

The present invention also features the use of RNA interference (RNAi) to inhibit expression of a soluble endoglin polypeptide or a fragment thereof. RNA interference (RNAi) is a recently discovered mechanism of post-transcriptional gene silencing (PTGS) in which double-stranded RNA (dsRNA) corresponding to a gene or mRNA of interest is introduced into an organism resulting in the degradation of the corresponding mRNA. In the RNAi reaction, both the sense and anti-sense strands of a dsRNA molecule are processed into small RNA fragments or segments ranging in length from 16 to 23 nucleotides (nt) and have 2-nucleotide 3' tails. Alternatively, synthetic dsRNAs, which are 21 to 23 nt in length and have 2-nucleotide 3' tails can be synthesized, purified, and used in the reaction. These 21 to 23 nt dsRNAs are known as "guide RNAs" or "short interfering RNAs" or "siRNAs."

The siRNA duplexes then bind to a nuclease complex composed of proteins that target and destroy endogenous mRNAs having homology to the siRNA within the complex. Although the identity of the proteins within the complex remains unclear, the function of the complex is to target the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene. siRNAs can also be chemically synthesized or obtained from a company that chemically synthesizes siRNAs (e.g., Dharmacon Research Inc., Pharmacia, or ABI).

The specific requirements and modifications of dsRNA are known in the art and are described, for example, in PCT Publication No. WO 01/75164 and in U.S. Patent Application Publication No. 20060067937 and PCT Publication No. WO 06/034507 (each incorporated herein by reference).

The administration of the above antibodies, inhibitory nucleic acids, and small compounds may be combined with methods to decrease sFlt-1 levels or to increase VEGF or P1GF levels, or decrease s-Flt-1 levels as described in PCT Publication Nos. WO 04/008947, WO 07/143,023, and WO 08/030,283, and U.S. Patent Publication Nos. 20040126828 and 20050170444 (each incorporated by reference). In addition, any compound that increases the level or biological activity of TGF-β, eNOS, and/or PGI2 are useful in the methods of the invention. Purified TGF-β family proteins include any protein with an amino acid sequence that is homologous, more desirably, substantially identical to the amino acid sequence of TGF-β1 (Cat #240-B-002) and human TGF-β3 (Cat #243-B3-002) from R & D Systems, MN. Preferred TGF-β family proteins useful in the methods of the invention will have the ability to bind soluble endoglin polypeptide. Cyclosporin may also be used at a dosage of 100-200 mg twice a day to stimulate TGF-β1 production. NOS activity may be increased using purified NOS (e.g., eNOS), nucleic acids encoding eNOS, statins, vanadate, hepatocyte growth factor, phosphinositide 3-kinase (PI3K), Akt, VEGF, TGF-β1, or any other compound that increases eNOS Ser 1177 phosphorylation or Thr 495 dephosphorylation or both. Compounds the increase the biological activity of NOS can be administered in combination with L-arginine or a nitric oxide donor (e.g., sodium nitroprusside, nitroglycerin, isosorbid-mononitrate, and isosorbo dinitrate). Compounds that increase the level or activity of PGI2 may also be administered (e.g., PGI2 mimetics, iloprast, cicaprost, and aspirin).

Any of the above compounds that can be used to treat a soluble endoglin-mediated disorder may be used alone or in combination with one or more additional agents. For example, one or more of the above described compounds may be administered in combination with any other standard pre-eclampsia or eclampsia therapy, e.g., those therapies described in U.S. Patent Application Publication Nos. 2004/0126828, 2005/0025762, 2005/0170444, 2006/0067937, and 2007/0104707, and PCT Publication Nos. WO 04/008946, WO 05/077007, WO 06/034507, WO 07/143,023, and WO 08/030,283 (each incorporated by reference). It will be understood by the skilled artisan that any combination of any of these agents can be used for this purpose. For example, an antibody that specifically binds to the soluble endoglin polypeptide of the invention or an antibody-binding fragment thereof can be administered in combination with VEGF. In another example, a compound that increases TGF-β1 levels or activity can be administered in combination with a compound that increases VEGF or P1GF in order to target both the endoglin and the VEGF pathway. Alternatively, a combination of antibodies or antibody-binding fragments thereof against both soluble endoglin polypeptide of the invention and sFlt-1 may be used either directly or in an ex vivo approach (e.g., using a column that is lined with anti-soluble endoglin polypeptide and anti-s-Flt-1 antibodies and circulating the subject's blood through the column). Any of these combinations can further include the administration of a compound that increases NOS levels or activity, preferably eNOS, in order to regulate the pathway downstream of the respective receptors.

In addition, the invention provides for the use of any chronic hypertension medications used in combination with any of the therapeutic methods described above. For example, medications used for the treatment of hypertension during pregnancy include methyldopa, hydralazine hydrochloride, or labetalol may be used in combination with an antibody that specifically binds soluble endoglin polypeptides of the invention. For each of these medications, modes of administration and dosages are determined by the physician and by the manufacturer's instructions.

Soluble Endoglin-Preventive Disorders

The invention further provides compositions and methods for treating or preventing the likelihood of developing a soluble endoglin-preventive disorder in a subject including but not limited to a disorder where a decrease in the soluble endoglin levels (protein or mRNA) or the soluble endoglin biological activity has been detected or implicated in the pathogenesis of the disorder or where specific factors, such as TGF β or events (e.g. fibrosis, angiogenesis, immune activation) that can be inhibited or modulated by soluble endoglin, which contribute to the disorder. Non-limiting examples include fibrotic disorders of internal organs and the scarring of skin where TGF-β is a significant contributor, disorders characterized by excessive angiogenesis (e.g. hemangiomas, or pulmonary capillary hemagiomatosis) or abnormal growth of blood vessel such as cancer (e.g., cancer of the breast, prostate, colon, lung, head and neck, liver, kidney, renal system, and endometrium) and inflammatory and immune disorders (e.g. excessive TGF-β may be related to autoimmune diseases).

The term cancer embraces a collection of malignancies with each cancer of each organ consisting of numerous subsets. Typically, at the time of cancer diagnosis, "the cancer" consists in fact of multiple subpopulations of cells with diverse genetic, biochemical, immunologic, and biological characteristics. Benign or malignant growths of cancer are referred to as tumors. The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, mature B-cell acute lymphoblastic leukemia, chronic lymphocytic leukemia, prolymphocytic leukemia, or hairy cell leukemia), or lymphoma (e.g., non-Hodgkin's lymphoma, cutaneous T-cell lymphoma, or Hodgkin's disease). Solid tumors can be further separated into those of epithelial origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, endometrium, male genital organ, urinary organs, bladder, and skin. Solid tumors of non-epithelial origin include sarcomas, brain tumors, and bone tumors. While the methods of the invention can be used to treat any tumor or tumor metastasis where soluble endoglin can be used to modulate or inhibit the occurrence, growth, or metastasis of the tumor, a soluble endoglin polypeptide, fragment, derivative, or analog of the invention, a nucleic acid encoding a soluble endoglin polypeptide of the invention, or a small molecule that increases the expression level (polypeptide or mRNA) or a biological activity of a soluble endoglin polypeptide of the invention is preferably used for the treatment or prevention of cancers that have increased TGF-β levels or biological activity, particularly TGF-β1 or TGF-β3, or tumors that have angiogenic activity.

Of particular importance to the present invention are subjects diagnosed with and/or treated for a primary tumor, including prophylactic treatment of at-risk subjects, not yet diagnosed with metastatic disease or determined to lack metastatic disease, and those subjects otherwise predisposed to developing metastatic disease. The methods of the invention can be used to prevent the occurrence or re-occurrence of metastatic disease. Also included are subjects who have undergone treatment of metastasis or a possible metastasis in order to prevent or reduce metastatic disease. The methods of the invention can be used before, during, or after additional therapies to treat the primary tumor, the metastases, or the risk of either.

Compositions for treating or preventing a soluble endoglin-preventive disorder preferably contain any of the purified soluble endoglin polypeptides, fragments, derivatives, or analogs described above or a nucleic acid encoding such a soluble endoglin polypeptide (e.g., SEQ ID NO: 4). Compositions for treating or reducing the likelihood of developing a soluble endoglin-preventive disorder may also contain an agent that can increase the expression levels (polypeptide or mRNA) or a biological activity of a soluble endoglin polypeptide as described above. Non-limiting examples of soluble endoglin polypeptides and nucleic acids encoding these soluble endoglin polypeptides are described above.

Nucleic acids encoding soluble endoglin polypeptides, or fragments, derivatives, or analogs thereof (as described above) can also be used in methods for treating or reducing the likelihood of developing a soluble endoglin-preventive disease. The nucleic acids encoding a soluble endoglin polypeptide, fragment, derivative, or analog of the invention may be obtained using routine procedures in the art, e.g., recombinant DNA and PCR amplification. For any of the nucleic acid applications described herein, standard methods for administering nucleic acids can be used. Examples are described in U.S. Patent Application Publication No. 2006/0067937 and PCT Publication No. WO 06/034507 (each incorporated by reference).

Delivery of nucleic acids to endothelial cells can be used in the present invention for the delivery of nucleic acids encoding soluble endoglin polypeptides, fragments, derivatives, or analogs of the invention. These general techniques are described in U.S. Pat. Nos. 5,830,879 and 6,258,727 (each incorporated by reference).

Compounds useful in the methods of the invention will increase the presently described soluble endoglin polypeptide or nucleic acid (e.g., mRNA) expression levels, or increase at least one biological activity of a soluble endoglin polypeptide by at least 5%, 10%, 15%, 20%, 25%, 30%, 35%, 40%, 45%, 50%, 55%, 60%, 70%, 80%, 90%, or 95% or more. Soluble endoglin polypeptide expression level and biological activity can be determined using the assays described above.

The invention also includes mimetics, based on modeling the 3-dimensional structure of a polypeptide or peptide fragment and using rational drug design to provide potential inhibitor compounds with particular molecular shape, size, and charge characteristics. Following identification of a therapeutic compound, suitable modeling techniques known in the art can be used to study the functional interactions and design mimetic compounds which contain functional groups arranged in such a manner that they could reproduce those interactions. The designing of mimetics to a known pharmaceutically active compound is a known approach to the development of pharmaceuticals based on a lead compound. This might be desirable where the active compound is difficult or expensive to synthesize or where it is unsuitable for a particular method of administration, e.g., peptides are not well suited as active agents for oral compositions as they tend to be quickly degraded by proteases in the alimentary canal. Mimetic design, synthesis, and testing may be used to avoid randomly screening a large number of molecules for a target property. The mimetic or mimetics can then be screened to see whether they increase the presently described soluble endoglin polypeptide or nucleic acid levels or soluble endoglin polypeptide biological activity, and further optimization or modification can then be carried out to arrive at one or more final mimetics for in vivo or clinical testing.

The soluble endoglin can also be delivered to the subjects using autologous or non-autologous stem cells (e.g., mesenchymal stem cells) to express the soluble endoglin protein. The transgenic stem cells can be prepared and delivered to the subject using techniques known in the art.

For the treatment of cancer, the above described compositions may be administered in conjunction (e.g., before, after, during) with additional cancer therapies to prevent or reduce tumor growth or metastasis. Treatment therapies include but are not limited to surgery, radiation therapy, chemotherapy, immune therapy (e.g., cytokines, cancer-specific antibodies, interferons, and biologics), differentiating therapy, anti-angiogenic therapy, hormone therapy, or hyperthermia.

It should be noted that while soluble endoglin may inhibit TGF-β signaling or activity it may have the opposite effect in other cell types or with other members of TGF-β superfamily (e.g., BMPs or Activins) and in those cases, inhibitors of soluble endoglin, such as those described herein are useful.

In addition to the above compositions, one or more additional cancer therapeutic (e.g., one or more of an angiogenesis inhibitor, an anti-proliferative compound, or a chemotherapeutic compound) may be co-administered to a subject for treating or preventing the development or a soluble endoglin-preventive disorder. For example, the soluble endoglin polypeptides, fragments, derivatives, or analogs described herein may be formulated alone or in combination with any additional cancer therapies in a variety of ways that are known in the art. Such additional cancer therapies can be administered before, during, or after the administration of the soluble endoglin polypeptides, fragments, derivatives, or analogs of the invention. Non-limiting examples of angiogenesis inhibitors, anti-proliferative compounds, and chemotherapeutic compounds are described below.

Angiogenesis inhibitors, also known as anti-angiogenic agents, that may be used in combination with any of the above soluble endoglin polypeptides, fragments, derivatives, and analogs or soluble endoglin nucleic acids for treating a cancer include: an anti-angiogenic antibody (e.g., an antibody that binds VEGF-A or an antibody that binds a VEGF receptor and blocks VEGF binding (e.g., anti-VEGF antibody and those described in U.S. Patent Publication Nos. 2003/0175271, 2005/0186208, 2006/0030529, 2007/0025999, 2007/0036753, 2007/003654, 2007/0036755, 2007/0036790, 2007/0071718, 2007/0071748, and 2007/0071749; each incorporated by reference)), VEGF trap, soluble VEGF receptor (e.g., sFlt1 and those described in U.S. Pat. Nos. 5,712,380; 5,861,484; and 7,071,159; and U.S. Patent Publication Nos. 2003/0120038, 2005/0276808, and 2007/0037748; each incorporated by reference), endostatin, angiostatin, restin, tumstatin, TNP-470, 2-methoxyestradiol, thalidomide, antibodies that inhibit TGF-β biological activity, a peptide fragment of an anti-angiogenic protein, canstatin, arrestin, a VEGF kinase inhibitor (e.g., SU11248, PTK787, BAY 43-9006, 1,5-diarylbenzimidazoles, and the inhibitors disclosed in U.S. Pat. Nos. 6,448,277; 6,465,484; and 7,045,133; and U.S. Patent Publication Nos. 2005/0085637, 2005/0234083, 2005/0288515, 2006/0135501, 2006/0160861, 2006/0264425, and 2007/0015756; each incorporated by reference), CPTK787, SFH-1, an anti-angiogenic protein, thrombospondin-1, platelet factor-4, interferon-α, an agent that blocks TIE-1 or TIE-2 signaling, an agent that blocks PIH12 signaling, an agent that blocks an extracellular vascular endothelial (VE) cadherin domain, an antibody that binds to an extracellular VE-cadherin domain, tetracycline, penicillamine, vinblastine, cytoxan, edelfosine, tegafur or uracil, curcumin, green tea, genistein, resveratrol, N-acetyl cysteine, captopril, a COX-2 inhibitor, celecoxib, and rofecoxib. Preferred combinations will include a soluble endoglin polypeptide, fragment, derivative, or analog, or a soluble endoglin nucleic acid in combination with a VEGF inhibitor or VEGF antagonist as described above (e.g., bevacizumab, VEGF trap, sFlt1, or an antibody that specifically binds VEGF).

The dosage of the angiogenesis inhibitor will depend on other clinical factors such as weight and condition of the human or animal and the route of administration of the compound. For treating humans or animals, between approximately 0.5 mg/kg to 500 mg/kg body weight of the angiogenesis inhibitor can be administered. A more preferable range is 1 mg/kg to 100 mg/kg body weight with the most preferable range being from 2 mg/kg to 50 mg/kg body weight. Depending upon the half-life of the angiogenesis inhibitor in the particular animal or human, the angiogenesis inhibitor can be administered between several times per day to once a week. The methods of the present invention provide for single as well as multiple administrations, given either simultaneously or over an extended period of time.

In addition, the invention provides for the use of an anti-proliferative compound used in combination with any of the soluble endoglin polypeptides, fragments, derivatives, or analogs, or soluble endoglin nucleic acids of the invention for treating a cancer. Anti-proliferative compounds that may be used include taxol, troglitazone, an antibody that binds basic fibroblast growth factor (bFGF), an antibody that binds bFGF-saporin, a statin, an acetylcholinesterase (ACE) inhibitor, suramin, 17-beta-estradiol, atorvastatin, fluvastatin, lovastatin, pravastatin, simvastatin, cerivastatin, perindopril, quinapril, captopril, lisinopril, enalapril, fosinopril, cilazapril, ramipril, and a kinase inhibitor.

The dosage of the anti-proliferative compound depends on clinical factors such as weight and condition of the human or animal and the route of delivery of the compound. In general, for treating humans or animals, between approximately 0.1 mg/kg to 500 mg/kg body weight of the anti-proliferative compound can be administered. A more preferable range is 1 mg/kg to 50 mg/kg body weight with the most preferable range being from 1 mg/kg to 25 mg/kg body weight. Depending upon the half-life of the anti-proliferative compound in the particular animal or human, the compound can be administered between several times per day to once a week. The methods of the present invention provide for single as well as multiple administrations, given either simultaneously or over an extended period of time.

It should be noted that although each of the compounds is listed under a specific category of compounds, these categories are not meant to be limiting in scope. Many of the compounds possess more than one activity and can therefore be included under more than one category.

For each of the compounds listed, all of the modes of administration described herein can be used. As some of the compounds described have shown toxicity when administered orally or systemically, local administration can also be used. In general, percent composition of the compound will range from 0.05% to 50% weight for weight of compound to coating material used.

Doses and Modes of Administration

Techniques and dosages for administration of the above described compositions useful for the treatment or amelioration of a soluble endoglin-preventive disorder or a soluble endoglin-mediated disorder vary depending on the type of compound (e.g., chemical compound, small molecule, purified protein, antibody, antisense, RNAi, or nucleic acid vector) and are well known to those skilled in the art or are readily determined.

Any of the compositions described herein can be formulated and administered in a variety of ways, e.g., those routes known for specific indications, including, but not limited to, topically, orally, subcutaneously, intravenously, intracerebrally, intranasally, transdermally, intraperitoneally, intramuscularly, intrapulmonary, vaginally, rectally, intraarterially, intralesionally, parenterally, intraventricularly in the brain, or intraocularly. Any of the compositions described above can be in the form of a pill, tablet, capsule, liquid, or sustained-release tablet for oral administration; or a liquid for intravenous or subcutaneous, systemic administration; or a polymer or other sustained-release vehicle for local administration.

The provided compositions can be administered continuously by infusion, using a constant- or programmable-flow implantable pump, or by periodic injections. Sustained-release systems can also be used. Administration can be continuous or periodic. Semi-permeable, implantable membrane devices are also useful as a means for delivering any of the compositions of the invention (e.g., anti-soluble endoglin antibodies, soluble endoglin polypeptides, fragments, derivatives, or analogs, or soluble endoglin nucleic acids). For example, cells that secrete soluble endoglin polypeptide or a fragment of the invention can be encapsulated, and such devices can be implanted into a subject, for example, into a primary tumor (e.g., a head and neck, a pancreatic, or an esophageal cancer). In another embodiment, any of the above compositions (e.g., a soluble endoglin polypeptide, fragment, derivative, or analog, or soluble endoglin nucleic acid) is administered locally, e.g., by direct injections, and the injections can be repeated periodically. Such local administration is particularly useful in the prevention and treatment of local metastasis.

Therapeutic formulations are prepared using standard methods known in the art by mixing the active ingredient having the desired degree of purity with optional physiologically acceptable carriers, excipients, or stabilizers (Remington's Pharmaceutical Sciences ($20^{th}$ edition), Ed., A. Gennaro, 2000, Lippincott, Williams & Wilkins, Philadelphia, Pa.), in the form of lyophilized formulations or aqueous solutions. Acceptable carriers, include saline, or buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant. Preferred surfactants are non-ionic detergents. Preferred surfactants include Tween 20 and pluronic acid (F68). Suitable surfactant concentrations are between 0.005 to 0.02%.

In one exemplary in vivo approach, a composition containing soluble endoglin polypeptide of the invention is administered to a subject. The soluble endoglin polypeptide can be delivered systemically to the subject or directly to the target tissue (e.g., to a tumor or a tumor bed following surgical excision of the tumor), in order to prevent or reduce metastasis or to inhibit survival of any remaining tumor or metastases cells. The dosage required depends on the choice of the route of administration; the nature of the formulation; the nature of the subject's illness; the subject's size, weight, surface area, age, and sex; other drugs being administered; and the judgment of the attending physician.

Wide variations in the needed dosage are to be expected in view of the variety of compositions provided by the invention (e.g., soluble endoglin polypeptides, fragments, derivatives, and analogs, anti-soluble endoglin antibodies, compounds, and soluble endoglin nucleic acids) and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2, 3, 4, 5, 6, 7, 8, 9, 10, 15, 20, 25, 50, 100, 150, or more). Encapsulation of the composition (e.g., a composition containing a soluble endoglin polypeptide, fragment, derivative, antibody, or fragment thereof, or analog of the invention) in a suitable delivery vehicle (e.g., polymeric microparticles, nanoparticle, or implantable devices) may increase the efficiency of delivery, particularly for oral delivery.

Alternatively, a composition of the invention can be delivered to the appropriate cells in the subject. For example, a polynucleotide containing a nucleic acid sequence encoding a soluble endoglin polypeptide (as described above) can be directed to any cell in the body of the subject. In certain embodiments, expression of the coding sequence can be directed to a tumor or metastases. This can be achieved by, for example, the use of polymeric, biodegradable microparticle, nanoparticle, or microcapsule delivery devices known in the art.

A nucleic acid (e.g., a nucleic acid encoding a soluble endoglin polypeptide described herein or an antisense oligomer that is complementary to a sequence encoding a soluble endoglin polypeptide described herein) can be introduced into the cells by any means appropriate for the vector employed. Many such methods are well known in the art (Sambrook et al., supra, and Watson et al., Recombinant DNA, Chapter 12, 2nd edition, Scientific American Books, 1992). Examples of methods of gene delivery include liposome-mediated transfection, electroporation, calcium phosphate/DEAE dextran methods, gene gun, and microinjection.

The dosage and the timing of administering the compound depends on various clinical factors including the overall health of the subject and the severity of the symptoms. In general, once a soluble endoglin-mediated disorder or a soluble endoglin-preventive disorder, or a propensity to develop a soluble endoglin-mediated disorder or a soluble endoglin-preventive disorder has been detected, any of the methods for administering a composition of the invention can be used to treat or prevent further progression of the disorder. For example, continuous systemic infusion or periodic injection to the site of the disease of a composition provided by the invention (e.g., a soluble endoglin polypeptide, fragment, derivative, or analog, or a soluble endoglin nucleic acid) can be used to treat or prevent the disorder. Treatment can be continued for a period of time ranging from 1 day through the lifetime of the subject, more preferably 1 day to 7 days, 1 day to 1 month, 1 to 100 days, 1 day to 6 months, 1 day to 1 year, 1 month to 1 year, 1 day to 5 years, 1 day to 10 years, and most preferably 1 to 20 days. For treating subjects, between approximately 0.1 mg/kg to 500 mg/kg body weight of the composition (e.g., soluble endoglin polypeptide, fragment, derivative, or analog of the invention) can be administered. A more preferable range is 1 mg/kg to 50 mg/kg body weight with the most preferable range being from 1 mg/kg to 25 mg/kg body weight. Depending upon the half-life of the composition (e.g., soluble endoglin polypeptide, anti-soluble endoglin antibody, fragment, derivative, or analog of the invention) in the particular subject, the composition can be administered between several times per day to once a week. The methods of the present invention provide for single as well as multiple administrations, given either simultaneously, or over an extended period of time.

Treatment of a soluble endoglin-mediated disorder or a soluble endoglin-preventive disorder as described herein can be continued for a period of time ranging from 1 to 100 days, more preferably 1 to 60 days, and most preferably 1 to 20 days, or two or more (e.g., 3, 4, 5, 6, 7, 8, 9, 10, 11, or 12 months or more), or until the completion of pregnancy (when said subject is pregnant). The dosages will vary depending on each compound and the severity of the disorder, and may be titrated to achieve a steady-state blood serum concentration ranging from 1 to 25, 1 to 20 ng/ml, or 1 to 7 ng/ml soluble endoglin polypeptide.

Where sustained-release administration of composition (e.g., a soluble endoglin polypeptide, fragment, derivative, or analog of the invention) is desired in a formulation with release characteristics suitable for the treatment of any disease or disorder, microencapsulation is contemplated. Microencapsulation of recombinant proteins for sustained release has been successfully performed with human growth hormone (rhGH), interferon-γ (rhIFN-γ), interleukin-2, and MN rgp120 (see, for e.g., Johnson et al., *Nat. Med.*, 2:795-799, 1996; Yasuda, *Biomed. Ther.*, 27:1221-1223, 1993; Hora et al., *Bio/Technology*, 8:755-758, 1990; Cleland, "Design and Production of Single Immunization Vaccines Using Polylactide Polyglycolide Microsphere Systems," in "Vaccine Design: The Subunit and Adjuvant Approach," Powell and Newman, Eds., Plenum Press: New York, pp. 439-462, 1995; WO 97/03692; WO 96/40072; WO 96/07399; and U.S. Pat. No. 5,654,010; each incorporated by reference).

The sustained-release formulations may include those developed using poly(lactic-co-glycolic acid) (PLGA) polymer. The degradation products of PLGA, lactic and glycolic acids, can be cleared quickly within the human body. Moreover, the degradability of this polymer can be adjusted from months to years depending on its molecular weight and composition. See, Lewis, "Controlled release of bioactive agents from lactide/glycolide polymer," in M. Chasin and Dr. Langer (Eds.), Biodegradable Polymers as Drug Delivery Systems (Marcel Dekker: New York, pp. 1-41, 1990).

An anti-soluble endoglin antibody, soluble endoglin polypeptide, fragment, derivative, or analog for use in the present invention may also be modified in a way to form a chimeric molecule comprising soluble endoglin polypeptide, fragment, derivative, or analog fused to another, heterologous polypeptide or amino acid sequence, such as an Fc sequence (e.g., a soluble endoglin immunoadhesin), or an additional therapeutic molecule (e.g., a chemotherapeutic or cytotoxic agent).

The soluble endoglin polypeptide, fragment, derivative, or analog, or the soluble endoglin nucleic acid of the invention can be packaged alone or in combination with other therapeutic compounds as a kit (e.g., a chemotherapeutic agent, an angiogenesis inhibitor, or an anti-proliferative compound). Non-limiting examples include kits that contain, e.g., two pills, a pill, and a powder, a suppository, a liquid in a vial, two topical creams, etc.

The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

The diagnostic methods described herein and methods known in the art can be used to monitor a soluble endoglin-mediated disorder or a soluble endoglin-preventive disorder during therapy or to determine the dosages of therapeutic compounds. In one example, a therapeutic composition (e.g., an antibody that specifically binds to the soluble endoglin polypeptide of the invention) is administered to a subject having pre-eclampsia and the PAAI is determined during the course of therapy. If the PAAI is less than 20, preferably less than 10, then the therapeutic dosage is considered to be an effective dosage. In another example, a therapeutic compound is administered and the soluble endoglin anti-angiogenic index is determined during the course of therapy. In another example, diagnostic methods that utilize an antibody that specifically binds to the C-terminus of the soluble endoglin polypeptide (e.g., specifically binds to the sequence of SEQ ID NO: 2), or a fragment thereof (e.g., 3 amino acids, 4 amino acids, 5 amino acids, or 6 amino acids) may be used to monitor a soluble endoglin-mediated disorder or a soluble endoglin-preventive disorder during therapy or to determine the dosages of therapeutic compounds.

Ex Vivo Therapies

Ex vivo strategies can also be used for the treatment of a soluble endoglin-mediated disorder and a soluble endoglin-preventive disorder.

For the treatment of a soluble endoglin-preventive disorders, desirable ex vivo strategies involve transfecting or transducing cells obtained from the subject with a nucleic acid encoding a soluble endoglin polypeptide or fragment of the invention. The transfected or transduced cells are then returned to the subject. The cells can be any of a wide range of types including, without limitation, hematopoietic cells (e.g., bone marrow cells, macrophages, monocytes, dendritic cells, T-cells, or B-cells), fibroblasts, epithelial cells, endothelial cells, keratinocytes, or muscle cells. Such cells act as a source of a soluble endoglin polypeptide or fragment for as long as they survive in the subject. Alternatively, tumor cells (e.g., any of those listed herein), preferably obtained from the subject, but potentially from an individual other than the subject, can be transfected or transformed by a vector encoding a soluble endoglin polypeptide or fragment of the invention. The tumor cells, preferably treated with an agent (e.g., ionizing irradiation) that ablates their proliferative capacity, are then introduced into the patient, where they secrete an exogenous soluble endoglin polypeptide or fragment.

The ex vivo methods include the steps of harvesting cells from a subject, culturing the cells, transducing them with an expression vector, and maintaining the cells under conditions suitable for expression of the soluble endoglin polypeptide or fragment of the invention. These methods are known in the art of molecular biology. The transduction step is accomplished by any standard means used for ex vivo gene therapy including calcium phosphate, lipofection, electroporation, viral infection, and biolistic gene transfer. Alternatively, liposomes or polymeric microparticles can be used. Cells that have been successfully transduced can then be selected, for example, for expression of the coding sequence or of a drug resistance gene. The cells may then be lethally irradiated (if desired) and injected or implanted into the patient.

For the treatment of soluble endoglin-mediated disorders, desirable ex vivo strategies can also involve plasmapheresis using a column or resin that contains antibodies that specifically bind the soluble endoglin polypeptides or fragments described herein (e.g., antibodies that bind to the C-terminal sequence of SEQ ID NO: 2), or a fragment thereof (e.g., 3 amino acids, 4 amino acids, 5 amino acids, or 6 amino acids). In these methods, the blood plasma from a patient having a soluble endoglin-mediated disorder is removed from the subject, passed through a column that contains antibodies that specifically bind a soluble endoglin polypeptide of the invention, and returned to the subject. This technique results in the removal of soluble endoglin polypeptide (as described herein) from a subject suffering from a soluble endoglin-mediated disorder.

Subject Monitoring
Soluble Endoglin-Mediated Disorders

The disease state or treatment of a subject having a soluble endoglin-mediated disorder as described herein (e.g., pre-eclampsia, eclampsia, or a predisposition to such a disorder) can be monitored using the diagnostic methods described herein and the methods known in the art. For example, elevated soluble endoglin polypeptide present in a bodily fluid, such as blood, serum urine, plasma, amniotic fluid, or CSF, can be monitored, wherein elevated levels of soluble endoglin polypeptide of the invention indicate that the subject has a soluble endoglin-mediated disorder or a predisposition for developing a soluble endoglin-mediated disorder. The soluble endoglin polypeptide described herein may be monitored in addition to the expression levels of sFlt-1, VEGF, PlGF, TGF-β, or eNOS polypeptide or nucleic acid, or PGI2 (see, diagnostic methods described in WO 08/030,283). Such monitoring may be useful, for example, in assessing the efficacy of a particular drug in a subject or in assessing disease progression. Therapeutics that decrease (e.g., by at least 5%, 10%, 15%, 20%, 25%, 30%, 40%, 50%, 60%, 70%, 80%, 90%, or even 100%) the expression (protein or mRNA) or a biological activity of a soluble endoglin polypeptide or fragment of the invention are taken as particularly useful for the treatment of a soluble endoglin-mediated disorder. Non-limiting methods for the monitoring of soluble endoglin mediated disorders (e.g., pre-eclampsia and eclampsia) are described in WO 08/030,283 (incorporated by reference). Desirably, the treatment of a subject having a soluble endoglin-mediated disorder results in at least a 10% decrease (e.g., at least a 15%, 20%, 25%, 30%, 35%, 40%, 45%, 50%, 55%, 60%, 65%, 70%, 75%, 80%, 85%, 90%, 95%, or even 100% decrease) in the severity of one or more (e.g., 2, 3, 4, 5, or 6) symptoms of a soluble endoglin-mediated disorder. Non-limiting examples of symptoms of a soluble endoglin-mediated disorder include high blood pressure, proteinuria, blurred vision, blindness, abdominal pain, excessive bruising, headaches, excessive swelling, excessive weight gain, vaginal bleeding, cramping, decreased fetal movement, malaise, nausea, paresthesia, seizure, intravascular coagulation, reduced fetal size, fever, chills, sweats, dry cough, muscle pain, and enlarged spleen.

Soluble Endoglin-Preventive Disorders

The disease state or treatment of a subject having a soluble endoglin-preventive disorder (e.g., cancer, cerebral arteriovenous malformations, cardiovascular disorders, and inflammatory disorders) can be monitored using the diagnostic methods described herein and the methods known in the art. For example, a subject receiving treatment may be monitored for an increase (e.g., at least 5%, 10%, 15%, 20%, 30%, 40%, 50%, 60%, 70%, or 80% increase) in the expression of a soluble endoglin polypeptide or nucleic acid of the invention or for an increase (e.g., at least 5%, 10%, 15%, 20%, 30%, 40%, 50%, 60%, 70%, or 80% increase) in a biological activity of a soluble endoglin polypeptide. In one example, the soluble endoglin biological activity includes antagonism of TGF-β signaling. An increase in the expression of a soluble endoglin polypeptide or nucleic acid of the invention, or an increase in a biological activity of a soluble endoglin polypeptide indicates successful treatment of an individual having a soluble endoglin-preventive disorder. Additionally, a subject receiving treatment for a soluble endoglin-preventive disorder may also be monitored using methods known in the art. Desirably, the treatment of a subject having a soluble endoglin-preventive disorder results in at least a 10% decrease (e.g., at least a 15%, 20%, 25%, 30%, 35%, 40%, 45%, 50%, 55%, 60%, 65%, 70%, 75%, 80%, 85%, 90%, 95%, or even 100% decrease) in the severity of one or more (e.g., 2, 3, 4, 5, or 6) symptoms of a soluble endoglin-preventive disorder. Non-limiting examples of symptoms of a soluble endoglin-preventive disorder include without limitation headaches, seizures, intracranial hemorrhage, loss of consciousness, nausea, vomiting, incontinence, blurred vision, hemiparesis, aphasia, angina, shortness of breath, heart palpitations, faster heartbeat, weakness or dizziness, sweating, persistent cough, blood-tinged saliva, diarrhea, blood in stool, anemia, breast lump or discharge, lumps in the testes, change in urination, blood in urine, hoarseness, swollen glands, change in wart or mole, indigestion or difficulty swallowing, vaginal bleeding or discharge, unexpected weight loss, night sweats, fever, skin color changes, itching in anal or genital area, non-healing sores, headaches, back pain, pelvic pain, and bloating.

The above symptoms of a soluble endoglin-mediated disorder and a soluble endoglin-preventive disorder can be monitored by a physician and the dosage and administration of one of more therapeutic compounds provided by the present invention may be adjusted based on the evaluation of these symptoms by the physician.

Diagnostic Assays and Kits
Soluble Endoglin-Mediated Disorders

The invention further provides methods for diagnosing a subject as having a soluble endoglin-mediated disorder or a predisposition for developing a soluble endoglin-mediated disorder. A diagnostic test measuring soluble endoglin polypeptide having a soluble endoglin biological activity and containing a sequence that is at least 70% identical (e.g., at least 71%, 72%, 73%, 74%, 75%, 80%, 81%, 82%, 83%, 84%, 85%, 90%, 95%, 96%, 97%, 98%, 99%, or 100% identical) to the sequence of SEQ ID NO: 2, or a fragment thereof (e.g., 3 amino acids, 4 amino acids, 5 amino acids, or 6 amino acids), optionally further measuring sFlt1 and free PlGF is useful for the detection and monitoring of a person having, or having a predisposition for developing, a soluble endoglin-mediated disorder. One example of an antibody useful for any of the diagnostic methods and kits of the invention is an antibody (e.g., a polyclonal antibody) that recognizes an epitope comprising a sequence that is at least 70% identical (e.g., at least 71%, 72%, 73%, 74%, 75%, 80%, 81%, 82%, 83%, 84%, 85%, 90%, 95%, 96%, 97%, 98%, 99%, or 100% identical) to the sequence of SEQ ID NO: 2, or a fragment thereof (e.g., 3 amino acids, 4 amino acids, 5 amino acids, or 6 amino acids). In one embodiment, the antibody is C-5144 or an antibody that competes with C-5144 for binding to soluble endoglin.

The diagnostic test may further measure the levels of free VEGF, TGF-β family members (preferably, TGF-β1 or TGF-β3), free activin-A, BMP2, BMP7, NOS (preferably eNOS), or PGI2, either alone or in any combination thereof. An alteration in the levels of any of these proteins is diagnostic of a soluble endoglin-mediated disorder (e.g., pre-eclampsia or eclampsia) (see, e.g., the diagnostic assays described in WO 08/030,283; incorporated by reference). In one example, a decrease in the levels of free BMP2, BMP7, or activin-A indicates that a subject has or has a predisposition for developing a soluble endoglin-mediated disorder (e.g., a pregnancy related hypertensive disorder).

Levels of soluble endoglin polypeptide or a fragment of the invention, either free, bound, or total levels, are measured in a subject sample and used as an indicator of a soluble endoglin-mediated disorder, where increased levels of soluble endoglin polypeptide or a fragment thereof indicate that the subject has a soluble endoglin-mediated disorder or has a predisposition for developing a soluble endoglin-mediated disorder. The soluble endoglin polypeptide or fragment can include any of the soluble endoglin polypeptides or fragments described herein, and may include degradation products, enzymatic cleavage products of soluble endoglin, and the like. An antibody that specifically binds a soluble endoglin polypeptide or fragment (as described herein) may be used for the diagnosis of a soluble endoglin-mediated disorder or to identify a subject at risk of developing such a disorder. A variety of protocols for measuring an alteration in the expression of such polypeptides are known, including immunological methods (such as ELISAs and RIAs), and provide a basis for diagnosing a soluble endoglin-mediated disorder or identifying a subject at risk of developing a soluble endoglin-mediated disorder.

Increased levels of a soluble endoglin polypeptide or fragment as described herein are positive indicators of a soluble endoglin-mediated disorder. For example, if the level of a soluble endoglin polypeptide or fragment of the invention is increased relative to a control reference (e.g., an increase of at least 10%, 20%, 30%, 40%, 60%, 70%, 80%, or 90% or more or 2-fold, 3-fold, 4-fold, 5-fold, 6-fold, 10-fold, or more) or the level increases over time in one or more samples from a subject, this is considered a positive indicator of a soluble endoglin-mediated disorder. In one specific example, an increase in soluble endoglin levels of approximately 2-fold may be diagnostic of pulmonary hypertension or a propensity to develop pulmonary hypertension. Additionally, any detectable alteration in levels of sFlt-1, VEGF, or P1GF relative to normal levels is indicative of a soluble endoglin-mediated disorder or the propensity to develop a soluble endoglin-mediated disorder (see, e.g., the diagnostic assays described in WO 08/030,283; incorporated by reference). Normally, circulating serum concentrations of soluble endoglin polypeptide range from 0-10 or 2-7 ng/mL (non-pregnant subjects) and 10-20 ng/mL (pregnant subjects). Elevated serum levels, greater than 15 ng/mL, preferably greater than 20 ng/mL, and most preferably greater than 25 ng/mL or more, of soluble endoglin polypeptide is considered a positive indicator of eclampsia or pre-eclampsia. Levels of soluble endoglin ranging from about 7 to about 12 ng/ml in sera from non-pregnant subjects is generally an indicator of primary and/or secondary pulmonary arterial hypertension.

In one embodiment, the level of soluble endoglin is measured in combination with the level of a sFlt-1, VEGF, or P1GF polypeptide or nucleic acid, or any combination thereof. Methods for the measurement of sFlt-1, VEGF, and P1GF are described in U.S. Patent Application Publication Numbers 2004/0126828, 2005/0025762, and 2005/0170444 and PCT Publication Numbers WO 2004/008946 and WO 2005/077007 (each incorporated by reference in their entirety). An increase in the level of sFlt-1 polypeptide or nucleic acid level, or a decrease in VEGF and P1GF polypeptide or nucleic acid levels indicate that the subject has an a soluble endoglin-mediated disorder or has a predisposition for developing a soluble endoglin-mediated disorder. In pregnancy-related hypertensive disorders, additional criteria, such as the body mass index (BMI) of the mother and the gestational age of the fetus is also measured and included in the diagnostic metric.

In another embodiment, the level of TGF-β1, TGF-β3, or eNOS polypeptide or nucleic acid is measured in combination with the level of a soluble endoglin or fragment, sFlt-1, VEGF, or P1GF polypeptide or nucleic acid of the invention. Antibodies useful for the measurement of TGF-β1 and TGF-β3 polypeptide levels are commercially available, for example, from Abcam, Abgent, BD Biosciences Pharmingen, Chemicon, GeneTex, and R&D Systems. The level of $PGI_2$ can also be used in combination with the level of any of the above polypeptides. $PGI_2$ levels can be determined, for example, using the $PGI_2$ receptor as a binding molecule in any of the diagnostic assays described above, or using, for example, the urinary prostacyclin colorimetric ELISA kit (Assay Designs). A decrease in $PGI_2$ levels indicates that the subject has a soluble endoglin-mediated disorder or has a predisposition for developing a soluble endoglin-mediated disorder. Antibodies useful for the measurement of eNOS polypeptide levels are commercially available, for example, from Research Diagnostics Inc., Santa Cruz, Cayman Chemicals, and BD Biosciences.

In another embodiment, the biological activity of any one or more of TGF-β1, TGF-β3, or eNOS polypeptide is measured in combination with the expression level of soluble endoglin of the invention (protein or mRNA) or a biological activity of soluble endoglin polypeptide or fragment, and the expression level of a sFlt-1, VEGF, or P1GF polypeptide. A decrease in the biological activity of TGF-β1, TGF-β3, or eNOS is a positive indicator of a soluble endoglin-mediated disorder (e.g., pre-eclampsia or eclampsia). The biological activity can be measured, for example using an assay for enzymatic activity or for the downstream signaling activity. In one example, the enzymatic activity of eNOS is determined by measuring citrulline conversion and a decrease in the enzymatic activity of eNOS is a positive indicator of a soluble endoglin-mediated disorder (e.g., pre-eclampsia or eclampsia).

Additional metrics may be used to diagnose a person as having a soluble endoglin-mediated disorder. Examples of metrics that may be used include PAAI (sFlt-1/VEGF+P1GF); anti-angiogenic index: (sFlt-1+0.25 (soluble endoglin polypeptide))/P1GF; (soluble endoglin+sFlt-1)/P1GF; and sFlt-1×soluble endoglin polypeptide or fragment. These metrics are described in WO 04/008946; WO 05/07707; and WO 06/034507 (each incorporated by reference).

In an example for the diagnosis of pregnancy-related hypertensive disorder (e.g., pre-eclampsia or eclampsia), the levels of sFlt-1 and a soluble endoglin polypeptide or fragment of the invention in the first and second trimesters is measured in a subject, and the delta value of sFlt1×soluble endoglin (sEng) is calculated in each trimester using the following equation: [dproduct=(sFlt1×sEng) in the second trimester—(sFlt1×sEng) in the first trimester], where a value greater than 0, 1, 2, or more, including fractions thereof (e.g., a positive value) is a diagnostic indicator of pre-eclampsia or eclampsia. A positive value can also be an indicator of preterm pre-eclampsia. Such a measurement can be taken on numerous occasions during the first and second trimesters and the dproduct can be followed over time. In addition, the dproduct of the sFlt-1 level (dsFlt-1) and the sEng level (dsEng) alone can also be calculated between the first and second trimesters, where a value greater than 0, 1, 2, or more, including fractions thereof (e.g., a positive value) for (dsFlt-1) or (dsEng) is a diagnostic indicator of pre-eclampsia or eclampsia. In addition, the metric can further include the level of TGF-β1, TGF-β3, PGI$_2$, or eNOS polypeptide. Any of the metrics can further include the BMI of the mother or the gestational age of the infant.

Standard methods may be used to measure levels of the soluble endoglin polypeptides or fragments described herein, free VEGF, free P1GF, sFlt-1, TGF-β1, TGF-β3, PGI$_2$, or eNOS polypeptide in any bodily fluid, including, but not limited to, urine, serum, plasma, saliva, amniotic fluid, or cerebrospinal fluid. Such methods include immunoassay, ELISA, western blotting using antibodies directed to soluble endoglin polypeptides or fragments, free VEGF, free P1GF, sFlt-1, TGF-β1, TGF-β3, PGI$_2$, or eNOS polypeptide and quantitative enzyme immunoassay techniques such as those described in Ong et al. (*Obstet. Gynecol.* 98:608-611, 2001) and Su et al. (*Obstet. Gynecol.,* 97:898-904, 2001). ELISA is the preferred method for measuring levels of a soluble endoglin polypeptide or fragment of the invention, VEGF, P1GF, sFlt-1, TGF-β1, TGF-β3, PGI$_2$, or eNOS polypeptide. Preferably, a soluble endoglin polypeptide or fragment described herein is measured alone or in combination with any one or more of the remaining polypeptides. For any of the diagnostic methods described herein, the soluble endoglin polypeptide is measured using an anti-soluble endoglin antibody of the invention including those that bind to an epitope that includes SEQ ID NO: 1 or SEQ ID NO: 2 or fragments thereof.

The measurement of any of the nucleic acids or polypeptides described herein can occur on at least two different occasions and an alteration in the levels as compared to normal reference levels over time can be used as an indicator of a soluble endoglin-mediated disorder or the propensity to develop such a disorder.

In one example, the level of a soluble endoglin polypeptide or fragment, or a soluble endoglin nucleic acid of the invention present in the bodily fluids of a subject having a soluble endoglin-mediated disorder or having a propensity to develop such a disorder may be increased by as little as at least 5% (e.g., at least 10%, 15%, 20%, 25%, 30%, 35%, 40%, 45%, 50%, 60%, 70%, 80%, 90%, 95%, 96%, 97%, 98%, or 99% or more) relative to levels in a normal control subject or relative to a previous sampling obtained from the same bodily fluid of the same subject. In another example, the level of a soluble endoglin polypeptide, fragment, or nucleic acid of the invention in the bodily fluids of a subject having a soluble endoglin-mediated disorder or having a propensity to develop such a disorder may be altered by as little as at least 5% (e.g., at least 10%, 15%, 20%, 25%, 30%, 35%, 40%, 45%, 50%, 55%, 60%, 70%, 80%, 90%, 95%, 96%, 97%, 98%, or 99% or more) over time from one measurement to the next.

The level of sFlt-1, VEGF, or P1GF measured in combination with the level of a soluble endoglin polypeptide, fragment, or nucleic acid of the invention in the bodily fluids of a subject having a soluble endoglin-mediated disorder or having the propensity to develop such a disorder may be altered by as little as at least 5% (e.g., at least 10%, 15%, 20%, 25%, 30%, 35%, 40%, 45%, 50%, 55%, 60%, 70%, 80%, 90%, 95%, 96%, 97%, 98%, or 99% or more) relative to the level of sFlt-1, VEGF, or P1GF in a normal control. The level of sFlt-1, VEGF, or P1GF measured in combination with the level of a soluble endoglin polypeptide, fragment or nucleic acid of the invention in the bodily fluids of a subject having a soluble endoglin-mediated disorder or having the propensity to develop such a disorder may be altered by as little as at least 5% (e.g., at least 10%, 15%, 20%, 25%, 30%, 35%, 40%, 45%, 50%, 55%, 60%, 70%, 80%, 90%, 95%, 96%, 97%, 98%, or 99% or more) over time from one measurement to the next.

In one embodiment, a subject sample of a bodily fluid (e.g., urine, blood, plasma, serum, amniotic fluid, or cerebrospinal fluid) is collected from a subject prior to the onset of symptoms of a soluble endoglin-mediated disorder. In another example, the sample can be a tissue or cell collected from the subject prior to the onset of symptoms of a soluble endoglin-mediated disorder. Non-limiting examples of tissues and cells include placental tissue, placental cells, circulating endothelial cells, and leukocytes such as monocytes. In humans, for example, maternal blood serum samples are collected from the antecubital vein of pregnant women during the first, second, or third trimesters of the pregnancy. The assay may be carried out during the first trimester, for example, at 4, 6, 8, 10, or 12 weeks, or any interval therein, or during the second trimester, for example at 14, 16, 18, 20, 22, or 24 weeks, or any interval therein. In one example, the assay is carried out between 13 and 16 weeks of pregnancy. Such assays may also be conducted at the end of the second trimester or the third trimester, for example at 26, 28, 30, 32, 34, 36, or 38 weeks, or any interval therein. It is preferable that the level of a soluble endoglin polypeptide, fragment, or nucleic acid of the invention and/or any of the additional polypeptides described herein be measured twice during this period of time. For the diagnosis of post-partum pre-eclampsia or eclampsia, assays for a soluble endoglin polypeptide, fragment, or nucleic acid described herein may be carried out postpartum. For the diagnosis of a predisposition to pre-eclampsia or eclampsia, the assay is carried out prior to the onset of pregnancy or prior to the development of symptoms of pre-eclampsia or eclampsia. In one example, for the monitoring and management of therapy, the assay is carried out during the pregnancy after the diagnosis of pre-eclampsia, and/or during therapy.

In one particular example, serial blood samples can be collected from a subject and the level of a soluble endoglin polypeptide or fragment and/or any of the additional polypeptides of the invention determined by ELISA. In another example, a sample is collected during the second trimester and early in the third trimester and in increase in the level of a soluble endoglin polypeptide or fragment and/or any of the other polypeptides of the invention from the first sampling to the next is indicative of pre-eclampsia or eclampsia, or the propensity to develop either.

In veterinary practice, assays may be carried out at any time during the pregnancy, but are, preferably, carried out early in pregnancy, prior to the onset of pre-eclampsia symptoms. Given that the term of pregnancies varies widely between species, the timing of the assay will be determined by a veterinarian, but will generally correspond to the timing of assays during a human pregnancy.

The diagnostic methods described herein can be used individually or in combination with any other diagnostic method described herein or known in the art for a more accurate diagnosis of the presence of, severity of, or estimated time of onset of a soluble endoglin-mediated disorder. In addition, the diagnostic methods described herein can be used in combination with any other diagnostic methods determined to be useful for the accurate diagnosis of the presence of, severity of, or estimated time of onset of a soluble endoglin-mediated disorder.

The diagnostic methods described herein can also be used to monitor and manage a soluble endoglin-mediated disorder in a subject. In one example, a therapy is administered until the blood, plasma, or serum soluble endoglin polypeptide or fragment level is less than 25 ng/ml in pregnant subjects or less than 7-12 ng/ml in sera of subject suffering from PAH, or until the serum soluble endoglin polypeptide or fragment levels (or soluble endoglin binding protein, $PGI_2$, or eNOS level) return to the baseline level determined before onset of the a soluble endoglin-mediated disorder. In another example, if a subject is determined to have an increased level of soluble endoglin polypeptide or fragment of the invention relative to a normal control then the therapy can be administered until the serum P1GF level rises to approximately 400 pg/mL or a return to baseline level prior to onset of the soluble endoglin-mediated disorder. In this embodiment, the levels of soluble endoglin polypeptide or fragment described herein, sFlt-1, P1GF, VEGF, soluble endoglin binding protein, $PGI_2$, eNOS or any and all of these, are measured repeatedly as a method of not only diagnosing disease but monitoring the treatment and management of the soluble endoglin-mediated disorder.

Soluble Endoglin-Preventive Disorder

The invention further provides methods for diagnosing a subject as having a soluble endoglin-preventive disorder or having a predisposition for developing a soluble endoglin-preventive disorder. The diagnostic methods and kits provided by the invention require the measurement of a soluble endoglin polypeptide or fragment as described herein and optionally further require measuring sFlt1, free P1GF, free VEGF, TGF-β family members (preferably, TGF-β1 or TGF-β3), free activin-A, BMP2, BMP7, NOS (preferably eNOS), or PGI2, either alone or in any combination thereof (wherein increased levels of one or more of these additional proteins is indicative of a soluble endoglin-preventive disorder). An alteration in the levels of any of these additional proteins is diagnostic of a soluble endoglin-preventive disorder (e.g., cancer).

Levels of a soluble endoglin polypeptide or fragment described herein, either free, bound, or total levels, are measured in a subject sample and used as an indicator of a soluble endoglin-preventive disorder, where decreased levels of a soluble endoglin polypeptide or fragment indicate that the subject has a soluble endoglin-preventive disorder or has a predisposition for developing a soluble endoglin-preventive disorder. The soluble endoglin polypeptide or fragment can include any of the soluble endoglin polypeptides or fragments described herein, and may include degradation products, enzymatic cleavage products of soluble endoglin, and the like. An antibody that specifically binds a soluble endoglin polypeptide may be used for the diagnosis of a soluble endoglin-preventive disorder or to identify a subject at risk of developing such a disorder. One example of an antibody useful for the methods of the invention is an antibody (e.g., a polyclonal antibody) that recognizes an epitope comprising a sequence that is at least 70% identical (e.g., at least 71%, 72%, 73%, 74%, 75%, 80%, 81%, 82%, 83%, 84%, 85%, 90%, 95%, 96%, 97%, 98%, 99%, or 100% identical) to the sequence of SEQ ID NO: 2, or a fragment thereof (e.g., 3 amino acids, 4 amino acids, 5 amino acids, or 6 amino acids).

Decreased levels of a soluble endoglin polypeptide or fragment as described herein or increased levels of TGF-β1 or TGF-β3 are positive indicators of a soluble endoglin-preventive disorder. For example, if the level of soluble endoglin polypeptide or fragment of the invention is decreased relative to a control reference (e.g., decreased by at least 5%, 10%, 15%, 20%, 25%, 30%, 35%, 40%, 45%, 50%, 55%, 60%, 70%, 80%, 90%, or 99% or more relative to a control reference) or decreases over time in one or more samples from a subject, this is considered a positive indicator of a soluble endoglin-preventive disorder.

As described above, the levels of sFlt-1, VEGF, P1GF, TGF-β1, TGF-β3, eNOS, activin A, BMP2, BMP7, and $PGI_2$ may be measured using methods known in the art. In additional preferred embodiments, the physical symptoms of a soluble endoglin-preventive disorder are also determined by a physician.

Diagnostic Kits

The invention also provides diagnostic kits containing components to perform the diagnostic methods described above. For example, a diagnostic kit can include one or more binding agents (e.g., polypeptides and the anti-soluble endoglin antibodies of the invention) that specifically bind to the soluble endoglin polypeptides or fragment described herein and components for detecting, and more preferably evaluating, binding between the binding agent and the soluble endoglin polypeptide or fragment.

The diagnostic kits also generally include a label or instructions for the intended use of the kit components and a reference sample or purified proteins to be used to establish a standard curve. In one example, the kit contains instructions for the use of the kit for the diagnosis of a soluble endoglin-mediated disorder (e.g., pre-eclampsia or eclampsia) or a soluble endoglin-preventive disorder (e.g., cancer), or instructions for identifying a subject having a propensity to develop one of these disorders. In yet another example, the kit contains instructions for the use of the kit to monitor therapeutic treatment or dosage regimens for the treatment of a soluble endoglin-mediated disorder or a soluble endoglin-preventive disorder. The diagnostic kit may also include a label or instructions for the use of the kit to determine metric values (e.g., the PAAI or the soluble endoglin anti-angiogenesis index) of the subject sample (as described above) and instructions to compare the metric to a reference sample value. It will be understood that the reference sample values will depend on the intended use of the kit. For example, the sample can be compared to a normal reference value, wherein an increase in the PAAI, the soluble endoglin anti-angiogenesis index, or the soluble endoglin value is indicative of a soluble endoglin-mediated disorder (e.g., pre-eclampsia or eclampsia). In another example, the sample can be compared to a normal reference value, wherein a decrease in the PAAI, the soluble endoglin anti-angiogenesis index, or the soluble endoglin value is indicative of a soluble endoglin-preventive disorder (e.g., cancer). In another example, a kit used for therapeutic monitoring can have a reference PAAI, a soluble endoglin anti-angiogenesis index value, or a soluble endoglin value that is indicative of a soluble endoglin-mediated disorder (e.g., pre-eclampsia or eclampsia), wherein an decrease in the PAAI, the soluble endoglin anti-angiogenesis index value, or the soluble endoglin value of the subject sample relative to the reference sample can be used to indicate therapeutic efficacy or effective dosages of therapeutic compounds for the treatment of a soluble endoglin-mediated disorder. In an additional example, a kit used for therapeutic monitoring can have a reference PAAI, a soluble endoglin anti-angiogenesis index value, or a soluble endoglin value that is indicative of a soluble endoglin-preventive disorder (e.g., cancer), wherein an increase in the PAAI, the soluble endoglin anti-angiogenesis index value, or the soluble endoglin value of the subject sample relative to the reference sample can be used to indicate therapeutic efficacy or effective dosages of therapeutic compounds for the treatment of a soluble endoglin-preventive disorder. A standard curve of levels of a purified soluble endoglin polypeptide, fragment, or nucleic acid of the invention within the normal or positive reference range, depending on the use of the kit, can also be included.

Screening Assays

Compounds for the Treatment of an Soluble Endoglin-Mediated Disorder

As discussed above, the level of a soluble endoglin polypeptide, fragment, or nucleic acid of the invention is increased in a subject having a soluble endoglin-mediated disorder. Soluble endoglin compositions of the invention are useful for the high-throughput low-cost screening of candidate compounds to identify those molecules that modulate the expression of the soluble endoglin polypeptides, fragments, or nucleic acids described herein.

Any number of methods are available for carrying out screening assays to identify new candidate compounds that alter the expression of a soluble endoglin nucleic acid molecule described herein. Examples are described in detail in U.S. Patent Application Publication No. 2006/0067937 and PCT Publication No. WO 06/034507 (each incorporated by reference).

In one working example, candidate compounds may be screened for those that specifically bind to a soluble endoglin polypeptide, or fragment, described herein. Desirably, the candidate compounds specifically bind to a sequence that is at least 75% identical to the C-terminal sequence of SEQ ID NO: 2, or a fragment thereof (e.g., 3 amino acids, 4 amino acids, 5 amino acids, or 6 amino acids). The efficacy of such a candidate compound is dependent upon its ability to interact with such a soluble endoglin polypeptide, or fragment, described herein, or a functional equivalent thereof. Such an interaction can be readily assayed using any number of standard binding techniques and functional assays such as immunoassays or affinity chromatography based assays (e.g., those described in Ausubel et al., supra). In one embodiment, a soluble endoglin polypeptide, or fragment, of the invention is immobilized and compounds are tested for the ability to bind to the immobilized soluble endoglin polypeptide, or fragment, using standard affinity chromatography based assays. Compounds that bind to the immobilized soluble endoglin polypeptide, or fragment, of the invention can then be eluted and purified, and tested further for their ability to bind to the soluble endoglin polypeptide or fragment both in vivo and in vitro, or tested for their ability to inhibit a biological activity of a soluble endoglin polypeptide or fragment.

In another example, a candidate compound is tested for its ability to decrease a biological activity of a soluble endoglin polypeptide, or fragment, as described herein. For example, a candidate compound may be tested for its ability to decrease the binding of a soluble endoglin polypeptide, or fragment, to a growth factor, such as TGF-β1, TGF-β3, activin-A, BMP-2, BMP-7, and BMP-9. These binding assays can be performed in vivo or in vitro using methods known in the art (e.g., see, WO 08/030,283). Additional biological activities of a soluble endoglin polypeptide, or fragment, described herein can be measured using any of the assays for measuring a soluble endoglin biological activity described above or known in the art.

Compounds for the Treatment of an Soluble Endoglin-Preventive Disorder

Compounds capable of increasing the expression levels (protein or mRNA) or biological activity of a soluble endoglin polypeptide of the invention, useful for the treatment of a soluble endoglin-preventive disorder, may be identified from large libraries of both natural product or synthetic (or semi-synthetic) extracts, chemical libraries, or from polypeptide or nucleic acid libraries, according to methods known in the art. Those skilled in the field of drug delivery and development will understand that the precise source of test extracts or compounds is not critical to the screening procedure(s) of the invention.

Any number of methods are available for carrying out screening assays to identify new candidate compounds that modulate the expression or biological activity of a soluble endoglin polypeptide, fragment, or nucleic acid of the invention. Examples are described in detail in U.S. Patent Application Publication No. 2006/0067937 and PCT Publication No. WO 06/034507 (incorporated by reference).

The following examples are meant to illustrate the invention. They are not meant to limit the invention in any way.

EXAMPLES

Example 1

Identification and Characterization of Human Soluble Endoglin (HsEng)

Soluble receptors are important mediators that are generated by either proteolytic cleavage of membrane-anchored receptors or alternative pre-mRNA splicing, resulting in truncated molecules lacking a transmembrane and intracellular domains. While some of these receptors act as antagonists by retaining their ability to bind ligands, others intercalate or dimerize with their cell surface receptor counterparts to either enhance or impair signal transduction. We have previously reported on a 64 kD circulating form of Eng, which we termed soluble endoglin (sEng) and found that this protein was elevated 10-20-fold in the sera of patients with pre-eclampsia. Peptide analysis of purified sEng by mass spectrometry revealed sequences belonging to parts of the N-terminal extracellular region of the full-length transmembrane glycoprotein. Not knowing the exact amino acid sequence of this form of sEng, we used a recombinant Eng (rEng) protein, which consisted of the entire extracellular region of cell surface Eng (amino acids 25-586) to test its effects on endothelial cells. Using this approach, we demonstrated that rEng induced endothelial dysfunction by interfering with the ability of TGF-β1 to bind to its receptors and to regulate endothelial nitric oxide synthase (eNOS) activity. Taken together, rEng displayed marked anti-angiogenic properties and contributed to the pathogenesis of pre-eclampsia. However, despite numerous attempts, the putative C-terminal cleavage site of Eng was never identified and therefore the true identity and perhaps function of the 64 kD sEng protein still remains unknown.

We have discovered a previously unrecognized alternatively spliced human Eng mRNA transcript, which contains a unique 3' sequence and UTR (FIG. 2A). This novel Eng mRNA was found using total placental RNA isolated from patients with pre-eclampsia and a modified 5'-3' rapid amplification of cDNA ends (RACE) method.

Cell surface Eng consists of 14 exons spread over 40 kb on human chromosome 9. The HsEng mRNA transcript is generated by exon extension whereby exon 9b is "extended" by 372 bases into intron 10 (FIG. 2A). The resulting novel 1683-base Eng mRNA transcript preserves the same ATG start site as the full-length form of Eng and harbors a stop codon at position 1333 and 351 bp of 3' UTR giving rise to a predicted 444-amino acid protein (FIG. 2A). Given that this transcript encodes the same signal peptide, but not the transmembrane region of full-length Eng, this suggests that this novel mRNA encodes a secreted protein. Our quantifications of HsEng mRNA relative to 18S RNA levels using Taqman primer/probe sets, suggest that the HsEng transcript is expressed at high levels in human lung, placenta, uterus and testes (FIG. 2B). We have also recently cloned the mouse sEng homolog (MsEng), which is generated similarly to HsEng, and found that this transcript is also most abundant in the lung. These findings suggest that the regulation of these transcripts is conserved across species and underscore the potential importance of soluble endoglin in the lung.

Overexpression of sEng cDNA in bovine aortic endothelial cells gave rise to a stable protein in the conditioned media with an apparent molecular weight of ~64 kD under both non-reducing and reducing conditions (FIG. 3C). The detection of this specific band supported our notion that our newly cloned sEng mRNA likely encodes the ~64 kD protein previously isolated previously by our group in the sera of patients with preeclampsia. While a relatively small portion of sEng was also detected as a ~125 kD dimer, these results strongly suggest that sEng exists predominantly as a monomer.

Materials and Methods

3'RACE.

RNA of placentae from patients diagnosed with pre-eclampsia was isolated with Trizol (Invitrogen) according to guidelines provided by the manufacturer. Five micrograms of total RNA was reverse transcribed with Supercript III reverse transcriptase and oligo dT primer supplied in the Generacer 5'-3' RACE kit (Invitrogen). The cDNA was amplified using the gene-specific primer, 5'-atggaccgcggcacgctccctctg-3' and the 3' primer (5'-gctgtcaacgatacgctacgtaacg-3' supplied in the Generacer Kit) with the following PCR cycling parameters: 5 minutes 95° C. denaturation, 1 minute 65° C. annealing and 1 minute 72° C. extension for 40 cycles. The PCR product was run on a 1.2% agarose TAE gel and bands of interest were cut out, purified and subcloned into pCRII-TOPO (Invitrogen).

Human sEng mRNA Expression.

Relative levels of HsEng mRNA were determined by real-time quantitative RT-PCR (TaqMan protocol). TaqMan analysis was performed using an ABI Prism 7700 sequence detection system (Applied Biosystems). The PCR primers and TaqMan probe specific for HsEng mRNA were designed using Primer Express software 1.5. Primer and probe sequences were as follows: Forward primer, 5'-TGGTCAG-CAATGAGGTGATCA-3' (SEQ ID NO: 5); Reverse primer, 5'-ACCGTCCATCTCACCCGAA-3' (SEQ ID NO: 6); TaqMan Probe 5'-FAM-CAGTTTCCCGTCAGGCTCAC-CACC-TAMRA-3' (SEQ ID NO: 7). Eukaryotic 18S rRNA TaqMan PDAR (predeveloped TaqMan assay reagents) Endogenous Control reagent mix (Applied Biosystems) was used to amplify 18S rRNA as an internal control, according to the manufacturer's protocol.

Overexpression of Human sEng Protein.

The HsEng coding sequence (bases 1-1335) was subcloned downstream of the cytomegalovirus (CMV) promoter in the pcDNA-Hygro vector (Invitrogen). Bovine aortic endothelial cells (BECs) were grown in 6-well plates and transiently transfected with either the pcDNA-Hygro vector (pc-Empty) or that containing HsEng (pc-HsEng) using Effectene (Qiagen) according to the manufacturer's guidelines. After 48 hrs, the condition media and cells were harvested for analysis by IP-Western blot. The condition media was spun down at 1500 rpm for 5 minutes to remove cellular contaminants followed by another spin at 14000 rpm for 15 minutes. Cells were harvested as previously described (Toporsian et al. Circ Res 2005). The samples were precleared with protein G (GE Healthcare) and immunoprecipitated with the human endoglin monoclonal antibody, P4A4 (1:200 dilution, Santa Cruz). One quarter of the immunoprecipitates (IPs) was separated by SDS-PAGE under non-reducing or reducing conditions, transferred onto nitrocellulose and blotted with a separate Eng antibody (T-20, 1:200 dilution, Santa Cruz) directed at the N-terminus of the protein and Hrp-conjugated anti-mouse or -rabbit secondary antibodies. Bands were visualized by chemiluminence.

Example 2

Affinity Purified sEng-Specific Antibody

Extension of exon 9 into intron 10 gives rise to a novel C-terminus that is unique to sEng (see FIG. 2A). This sequence was therefore used as an immunogen to generate an affinity purified rabbit polyclonal antibody, which we have named C-5144. This antibody can specifically detect sEng in sera of patients with pre-eclampsia and should not recognize the recombinant (rEng) or transmembrane form of Eng (FIG. 3D) as the HsEng antigenic site is not present in the latter forms of the protein. Indeed, we were able to detect increased levels of HsEng in the sera of patients with pre-eclampsia suggesting that the sEng protein generally detected in normal and preeclamptic sera harbors the unique C-terminal sequence generated as a result of alternative pre-mRNA splicing. We believe that the HsEng described herein and the 64 kD protein previously detected in this disease is one and the same (FIG. 3D).

Materials and Methods

Generation of Affinity Purified sEng-Specific Antibody.

The sEng-specific peptide, -VRWTVTC- (SEQ ID NO: 2), was synthesized and injected into rabbits by personel at Open Biosystems, a subsidiary of ThermoFisher. Crude sera were analyzed for their ability to detect HsEng and selected for affinity purification. The affinity-purified rabbit polyclonal antibody, is referred to as C-5144. Sera from normal and patients with preeclampsia were spun at 14000 g for 15 minutes and 50 mL was immunoprecipitated with a human endoglin monoclonal antibody, P4A4 (1:200 dilution, Santa Cruz) as previously described (Toporsian et al. Circ. Res. 96:684-692 (2005), Venkatesha et at. Nat. Med. 12:642-649 (2006)). One quarter of the IPs was separated by SDS-PAGE under non-reducing conditions, transferred onto nitrocellulose and blotted with C-5144 (1:500) and Hrp-conjugated anti-rabbit secondary antibody. Bands were visualized by chemiluminence.

Example 3

Elevated HsEng Levels in Sera of PAH Patients

We hypothesized that the chronic and local production of HsEng in the lung may account for the manifestation of PAH in individuals irrespective of any germline mutations in genes encoding BMPR2 or ALK1. Given the importance of these receptors in endothelial cell survival and the potential perturbations of their activities by HsEng either directly or via its interaction with cell-surface endoglin, we reasoned that increased HsEng within the alveolar wall and surrounding microvasculature might be a critical event leading to the observed loss of capillaries, alveolar wall thickening and muscularization of arterioles in PAH. We have found significantly elevated HsEng levels in sera of patients with PAH (FIG. 4). Of note, HsEng detected in these serum samples had the same apparent molecular weight as our positive control, which consisted of the conditioned medium of HEK293T cells that were transfected with HsEng cDNA.

Materials and Methods

Sera from normal and patients with pulmonary arterial hypertension (PAH) were spun at 14000 g for 15 minutes and 50 mL was immunoprecipitated with a human endoglin monoclonal antibody, P4A4 (1:200 dilution, Santa Cruz) as previously described (Toporsian et. al. Circ. Res. 2005, Venkatesha Nat. Med. 2006). One quarter of the IPs was separated by SDS-PAGE under non-reducing conditions, transferred onto nitrocellulose and blotted with a separate Eng antibody (AF1097, 1:1000, R&D systems) directed at the N-terminus of the protein and Hrp-conjugated anti-goat secondary antibodies. Bands were visualized by chemiluminence and quantified by densitometry.

Example 4

HsEng Induces Signs of PAH in Rodents

Figure 5:
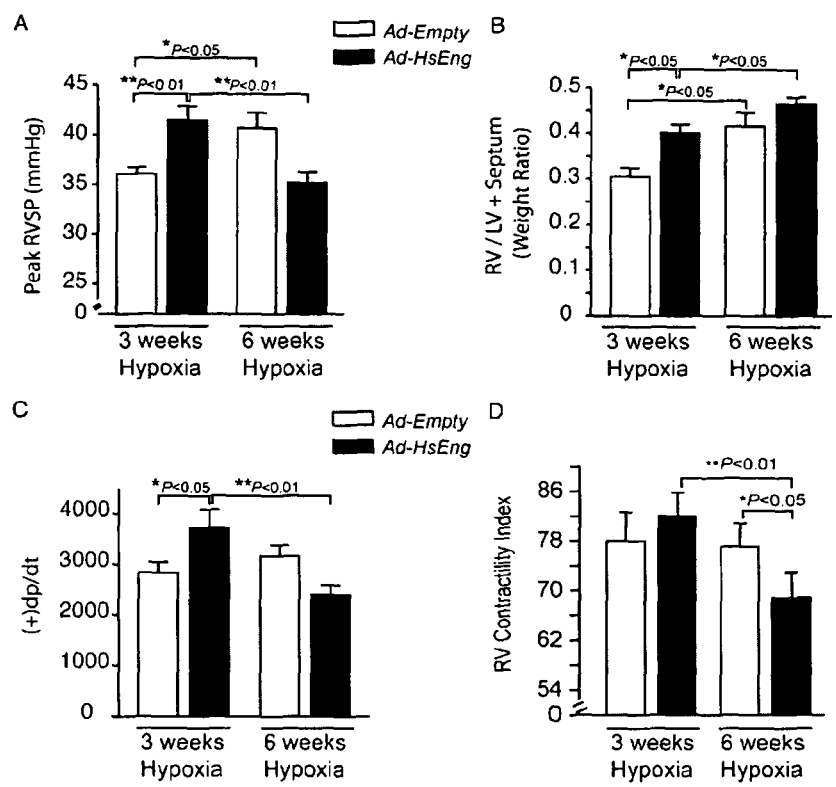
FIGS. 5A-5D are graphs showing the change in peak RVSP (5A), RV hypertrophy (5B), RV delta pressure/delta time (dp/dt) value (5C), and RV contractility index (5D) in mice inoculated with Ad-Empty (control) or Ad-HsEng and then exposed to hypoxic conditions for either 3 weeks or 6 weeks.

We tested whether or not HsEng is able to induce signs of PAH in rodents. We generated an adenovirus carrying the HsEng cDNA sequence downstream of a cytomegalovirus (CMV) promoter (Ad-HsEng) and inoculated mice with either Ad-HsEng or Ad-Empty by intra-tracheal nebulization. These mice were then exposed to hypoxia (12% $O_2$) for a period of 3 or 6 weeks. This route of adenovirus delivery was chosen to specifically target the lung and avoid secondary effects such as widespread systemic endothelial dysfunction resulting from intravenous injections, which can potentially influence our assessment of cardiopulmonary hemodynamics and histology. Mice exposed to chronic hypoxia after inoculation with Ad-HsEng, showed signs of accelerated disease progression including significantly elevated RVSP and RV hypertrophy compared to control mice treated with Ad-Empty and subsequently exposed to hypoxia (FIG. 5A, B). Interestingly, prolonged exposure to hypoxia (6 weeks) led to a significant drop in RVSP in the Ad-HsEng-treated group despite evidence of progressive RV hypertrophy (FIG. 5A, B). This observation was associated with a significant decrease in the RV delta pressure/delta time (dp/dt) value and RV contractility index in the Ad-HsEng-treated group exposed to hypoxia for 6 weeks (FIG. 5C, D). The gross physical behavior of these mice appeared more sluggish than that seen in mice in the control (Ad-Empty) group. Control mice exposed to hypoxia for 3 and 6 weeks displayed a gradual increase in RV pressure and hypertrophy, demonstrating a normal response to chronic hypoxia.

Example 5

Figure 6:
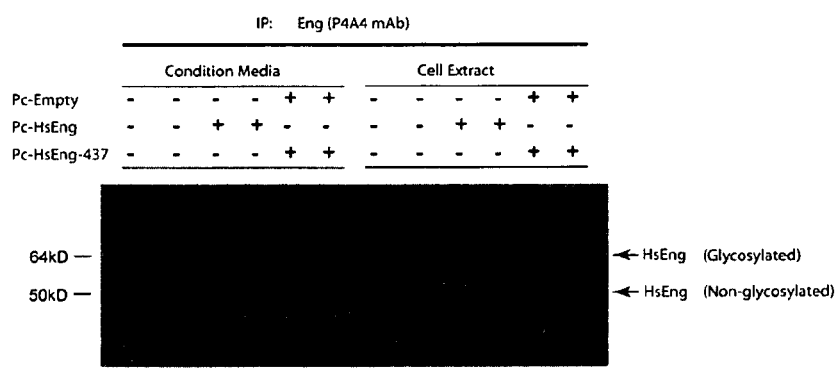
FIG. 6 is a representative IP-Western blot showing that cells transfected with pc-HsEng (expressing the 444 amino acid form of soluble endoglin) produced a stable and glycosylated 64 kD protein in the condition medium. A prominent band at ~50 kD was present in the corresponding cell extracts and likely represents the unglycosylated HsEng protein (expected: 49 kD). Cells transfected with HsEng-437 did not give rise to a 64 kD protein in the condition media, while a faint band was observed in the corresponding cell extracts at ~50 kD (unglycosylated protein).

C-Terminal Tail is Essential for HsEng Expression cDNA constructs as described below were used for expression of the HsEng protein. As shown in FIG. 6, cells transfected with pc-HsEng (which expresses amino acids 1-444 of soluble endoglin as shown in FIGS. 1 and 3B) produced a stable and glycosylated 64 kD protein in the condition medium. A prominent band at ~50 kD was present in the corresponding cell extracts and likely represents the unglycosylated HsEng protein (expected: 49 kD). Cells transfected with HsEng-437 (which lacks the 7 amino acid C-terminal tail) did not give rise to a 64 kD protein in the condition media, while a faint band was observed in the corresponding cell extracts at ~50 kD (unglycosylated protein). The 7 amino acid C-terminal sequence in HsEng-437 is necessary to enable the production of a properly folded, stable and secreted protein.

These findings suggest that an antibody, small molecule inhibitor or small inhibitory siRNA/miRNA that can disrupt the apparent protein-stabilizing role or expression of the 7aa c-terminal peptide can be potentially useful in altering the half-life and levels of HsEng in HsEng-dependent diseases. Previous reports have suggested the presence of a proteolytic cleavage site at position 437aa of cell surface endoglin (FIGS. 2A and 3B) that can potentially yield a truncated form of the protein. However, the expression of Endo-437 was very transient and is consistent with our current findings.

Materials and Methods

Using the pc-HsEng construct, Val438 was changed to the stop codon, UAG, by standard PCR-based site-directed mutagenesis using forward (5'-ctcatcaccacagcggtagagatgga-cagtcacg-3' (SEQ ID NO: 8)) and reverse (5'-cgtgactgtc-catctctaccgctgtggtgatgag-3' (SEQ ID NO: 9)) using the Quickchange protocol (Stratagene). The clone containing the specific mutation was sequenced and the mutated HsEng-437 cDNA insert was cut out by restriction digest and subcloned into an aliquot of the pcDNA-Hygro vector. The pc-empty, pc-HsEng and pc-HsEng-437 constructs were transiently transfected into human kidney epitheial (HEK) 293T cells using the transfection reagent, Fugene (Roche) according to the manufacturer's guidelines. After 48 hrs, the condition media and cells were harvested for analysis by IP-Western blot. The condition media was spun down at 1500 rpm for 5 minutes to remove cellular contaminants followed by another spin at 14000 rpm for 15 minutes. Cells were harvested as previously described (Toporsian et al. Circ Res 2005, supra). The samples were precleared with protein G (GE Healthcare) and immunoprecipitated with the human endoglin monoclonal antibody, P4A4 (1:200 dilution, Santa Cruz). One quarter of the immunoprecipitates (IPs) was separated by SDS-PAGE under non-reducing conditions, transferred onto nitrocellulose and blotted with a separate Eng antibody (AF1097, 1:1000, R&D systems) directed at the N-terminus of the protein and Hrp-conjugated anti-goat secondary antibodies. Bands were visualized by chemiluminence.

Example 6

Post-Translational Modification of HsEng

Figure 7:
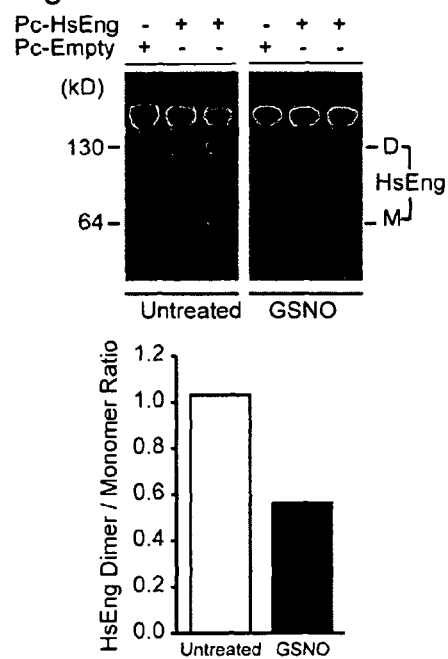
FIG. 7 shows a representative western blot and graph of immunoprecipitates from untreated samples and those treated with GSNO and subjected to biotin-switch. The expression of HsEng in HEK293T cells that do not normally express eNOS (enzyme that produces NO•), resulted in equal amounts of dimeric and monomeric HsEng (left panel). Ex vivo treatment of HsEng produced in HEK293T cells with the NO donor, GSNO, resulted in the S-nitrosylation of HsEng. S-nitrosylation of HsEng reduced the dimer/monomer ratio of this protein and may potentially impact its function.

The dimerization of certain secreted or cell surface proteins can protect them from digestion by proteases, thereby prolonging their half-life and steady-state levels. We have found that the overexpression of HsEng cDNA in bovine aortic endothelial cells (BECs), predominantly gives rise to a monomeric protein although some dimers could also be detected. S-nitrosylation of cysteines has quickly emerged as an important post-translational modification that can have profound effects on protein structure and function. This modification occurs when a cysteine thiol reacts with NO• in the presence of an electron acceptor to form an S—NO bond. As shown in FIG. 7, expression of HsEng in HEK293T cells that do not normally express eNOS (enzyme that produces NO•), resulted in equal amounts of dimeric and monomeric HsEng (left panel). Ex vivo treatment of HsEng produced in HEK293T cells with the NO donor, GSNO, resulted in the S-nitrosylation of HsEng. S-nitrosylation of HsEng reduced the dimer/monomer ratio of this protein and may potentially impact its function.

Materials and Methods

The pc-empty or pc-HsEng constructs were transiently transfected into human kidney epitheial (HEK) 293T cells using the transfection reagent, Fugene (Roche) according to the manufacturer's guidelines. After 48 hrs, the condition media were harvested, concentrated using 50K columns (Millipore) and immediately processed for immunoprecipitation as described below. In a separate set, concentrates were treated with the NO donor, GSNO (10 mM) for 1 hour and subjected to biotin-switch using the S-Nitrosylated Protein Detection Kit (Cayman Chemical) according to the manufacturer's guidelines. The biotinylated proteins were enriched using M-280 streptavidin dynabeads (Invitrogen protocol), precleared with protein G (GE Healthcare) and immunoprecipitated with the human endoglin monoclonal antibody, P4A4 (1:200 dilution, Santa Cruz). One quarter of the immunoprecipitates (IPs) was separated by SDS-PAGE under non-reducing conditions, transferred onto nitrocellulose and blotted with a separate Eng antibody (AF1097, 1:1000, R&D systems) directed at the N-terminus of the protein and Hrp-conjugated anti-goat secondary antibodies. Bands were visualized by chemiluminence and quantified by densitometry.

Example 7

Generation of pTRE-HsEng-HPRT Mice

Figure 8:
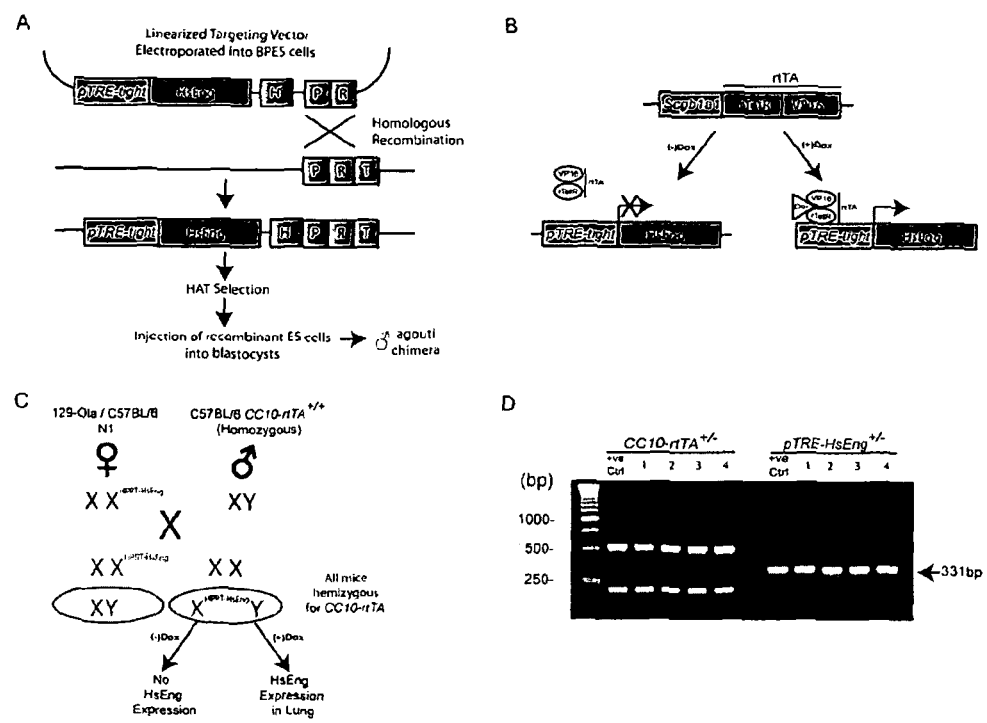
FIGS. 8A-8C show a schematic for the generation of the tetracycline inducible transgenic mouse.
FIG. 8D shows the results of genotyping of these mice using PCR primers. Shown is a 331 bp amplicon encompassing the distal end of pTRE-tight promoter and proximal end of the HsEng sequence.

We generated a tetracycline-inducible transgenic mouse by placing HsEng cDNA downstream of the minimal Tet-Responsive Element (TRE)-tight promoter and targeted this construct into the mouse hypoxanthine-guanine phosphoribosyl transferase (HPRT) locus. The HPRT locus is located within the X chromosome and has two important advantages for the targeting of transgenes. First, we have parent embryonic stem (ES, Ola/129-derived; agouti coat color) cells lacking a functional Hprt gene, which could be reconstituted by homologous recombination and selected in medium containing hypoxanthine, aminopterin, and thymidine (HAT). Second, the Hprt gene is ubiquitously expressed and the locus is transcriptionally favorable and free of the constraints of higher order gene regulation. ES cells were electroporated with linearized targeting vector and recombinant ES cells were selected in HAT medium, genotyped and chosen for injection into C57BL/6-derived blastocysts to generate male agouti mice displaying 80-100% chimerism (FIG. 8A). Mouse chimeras were mated with C57BL/6 female mice to generate F1 progeny. F1 female mice displaying agouti coat color are expected to have germline transmission of the transgenic X chromosome. Indeed, genotyping of these mice using PCR primers yielded a 331 bp amplicon encompassing the distal end of pTRE-tight promoter and proximal end of the HsEng sequence (FIG. 8D). We currently have female F1 mice (pTRE-HsEng-HPRT), which have been backcrossed with C57BL/6 males and given birth to pups (N1 generation). These mice will be an excellent resource in understanding the role of HsEng in various organs by crossing them with commercially available transgenic mice capable of organ-specific Dox-inducible expression.

In order to more closely replicate the adenovirus aerosolization experiments that have yielded promising preliminary results (FIG. 5A-D above), HsEng expression can be specifically targeted in lung bronchial and alveolar type II epithelial cells. To this end, female N1 progeny carrying the pTRE-HsEng transgene were crossed with male homozygous CC10-rtTA mice carrying the reverse tetracycline-controlled transactivator (rtTA) protein under the control of the rat secretagloblin (Scgbla1, family 1A, member 1) gene promoter (FIG. 8B, C). Using this breeding strategy, all progeny will be hemizygous for CC10-rtTA while 50% of male mice will be pTRE-HsEng/CCSP-rtTA bitransgenic and therefore capable of inducing HsEng expression in bronchial and type II lung epithelial cells when CC10-rtTA is expressed upon exposure to Dox, (1 mg/mL, drinking water) (FIG. 8D, showing 4 bitransgenic mice). Of note, rtTA-induced expression of a luciferase reporter under the regulation of a TRE promoter has been detected as early as embryonic day 12.5 in embryos from pregnant females treated with Dox (REF). Basal luciferase activity was negligible (<200 RLU) and maximal activity (>7000 RLU) was reached within 16 hours when exposed to Dox (REF). In all experiments, male mice can be used to circumvent potential silencing of our transgene, if it is inherited on an X chromosome destined for inactivation in female mice.

Preliminary studies indicate that these mice develop signs of PAH. These mice can also be tested with the HsEng-specific (C-5144) antibody to determine inhibition of the onset and progression of PAH in these mice, lending additional support to the therapeutic use of the anti-HsEng antibodies.

Example 7

TNF-α Increases HsEng Protein Expression from Endothelial Cells

The effects of TNF-α on HsEng expression were tested using human lung microvascular endothelial cells. As shown in FIGS. 10A and B, treatment of HMVEC-L with TNF-α does not induce any changes in HsEng mRNA levels (FIG. 9A), but increases HsEng protein levels in the condition media (FIG. 9B).

Materials and Methods

Human lung microvascular endothelial cells (HMVEC-L) were grown to confluence and treated with or without TNF α (50 ng/mL) for 24 hours. Cells were harvested and both RNA and proteins were isolated as previously described.

HsEng mRNA Expression

Relative levels of HsEng mRNA were determined by real-time quantitative RT-PCR (TaqMan protocol). TaqMan analysis was performed using an ABI Prism 7700 sequence detection system (Applied Biosystems). The PCR primers and TaqMan probe specific for HsEng mRNA were designed using Primer Express software 1.5. Primer and probe sequences were as follows: Forward primer, 5'-TGGTCAG-CAATGAGGTGATCA-3' (SEQ ID NO: 10); Reverse primer, 5'-ACCGTCCATCTCACCCGAA-3' (SEQ ID NO: 11); TaqMan Probe 5'-FAM-CAGTTTCCCGTCAGGCTCAC-CACC-TAMRA-' (SEQ ID NO: 12). Eukaryotic 18S rRNA TaqMan PDAR (predeveloped TaqMan assay reagents) Endogenous Control reagent mix (Applied Biosystems) was used to amplify 18S rRNA as an internal control, according to the manufacturer's protocol.

HsEng Protein Expression.

The condition media was spun down at 1500 rpm for 5 minutes to remove cellular contaminants followed by another spin at 14000 rpm for 15 minutes. Cells were harvested as previously described (Toporsian et al. Circ Res 2005). The samples were precleared with protein G (GE Healthcare) and immunoprecipitated with the human endoglin monoclonal antibody, P4A4 (1:200 dilution, Santa Cruz). One quarter of the immunoprecipitates (IPs) was separated by SDS-PAGE under non-reducing conditions, transferred onto nitrocellulose and blotted with a separate Eng antibody (AF1097, 1:1000, R&D systems) directed at the N-terminus of the protein and Hrp-conjugated anti-goat secondary antibodies. Bands were visualized by chemiluminence.

Other Embodiments

All publications, patents, and patent application publications cited in this specification are incorporated herein by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated antibody, or antigen-binding fragment thereof, that specifically binds to a human soluble endoglin polypeptide, wherein the antibody, or antigen-binding fragment, binds to an epitope corresponding to an amino acid sequence having at least 85% sequence identity to VRWTVTC (SEQ ID NO: 2).

2. The antibody or antigen-binding fragment of claim 1, wherein the antibody or antigen-binding fragment binds to the amino acid sequence of SEQ ID NO: 2.

3. The antibody or antigen-binding fragment of claim 1, wherein the antibody or antigen-binding fragment competes with the antibody C-5144 for binding to soluble endoglin.

4. A kit comprising:
   (a) the isolated antibody or antigen-binding fragment thereof of claim 1; and
   (b) a pharmaceutically acceptable carrier.

* * * * *

```
                        SEQUENCE LISTING

<160> NUMBER OF SEQ ID NOS: 12

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Arg Val Arg Trp Thr Val Thr Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Val Arg Trp Thr Val Thr Cys
1               5

<210> SEQ ID NO 3
<211> LENGTH: 444
<212> TYPE: PRT
<213> ORGANISM: Artificial Sequence
<220> FEATURE:
<223> OTHER INFORMATION: Synthetic Construct

<400> SEQUENCE: 3

Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
                20                  25                  30

Gln Pro Val Gly Pro Glu Arg Gly Glu Val Thr Tyr Thr Thr Ser Gln
            35                  40                  45

Val Ser Lys Gly Cys Val Ala Gln Ala Pro Asn Ala Ile Leu Glu Val
        50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
                100                 105                 110

Gly Ile Pro Leu His Leu Ala Tyr Asn Ser Ser Leu Val Thr Phe Gln
            115                 120                 125

Glu Pro Pro Gly Val Asn Thr Thr Glu Leu Pro Ser Phe Pro Lys Thr
        130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
                180                 185                 190
```

```
Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
    210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
        275                 280                 285

Gly Phe Lys Leu Pro Asp Thr Pro Gln Gly Leu Leu Gly Glu Ala Arg
    290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
        355                 360                 365

Thr Leu Val Leu Lys Lys Glu Leu Val Ala His Leu Lys Cys Thr Ile
    370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
            420                 425                 430

Ser Ser Pro Gln Arg Val Arg Trp Thr Val Thr Cys
        435                 440

<210> SEQ ID NO 4
<211> LENGTH: 1683
<212> TYPE: DNA
<213> ORGANISM: Artificial Sequence
<220> FEATURE:
<223> OTHER INFORMATION: Synthetic Construct

<400> SEQUENCE: 4
atggaccgcg gcacgctccc tctggctgtt gccctgctgc tggccagctg cagcctcagc        60
cccacaagtc ttgcagaaac agtccattgt gaccttcagc tgtgggccc cgagaggggc       120 gaggtgacat ataccactag ccaggtctcg aagggctgcg tggctcaggc ccccaatgcc       180
atccttgaag tccatgtcct cttcctggag ttcccaacgg gccgtcaca gctggagctg       240 actctccagg catccaagca aaatggcacc tggccccgag aggtgcttct ggtcctcagt       300
gtaaacagca gtgtcttcct gcatctccag gccctgggaa tcccactgca cttggcctac       360
aattccagcc tggtcacctt ccaagagccc cggggggtca acaccacaga gctgccatcc       420
ttccccaaga cccagatcct gagtgggca gctgagaggg ccccatcac ctctgctgct       480 gagctgaatg accccagag catcctcctc cgactgggcc aagcccaggg gtcactgtcc       540
ttctgcatgc tggaagccag ccaggacatg ggccgcacgc tcgagtggcg gccgcgtact       600
```

```
ccagccttgg tccggggctg ccacttggaa ggcgtggccg gccacaagga ggcgcacatc    660
ctgagggtcc tgccgggcca ctcggccggg ccccggacgg tgacggtgaa ggtggaactg    720
agctgcgcac ccggggatct cgatgccgtc ctcatcctgc agggtccccc ctacgtgtcc    780
tggctcatcg acgccaacca caacatgcag atctggacca ctggagaata ctccttcaag    840
atctttccag agaaaaacat tcgtggcttc aagctcccag acacacctca aggcctcctg    900
ggggaggccc ggatgctcaa tgccagcatt gtggcatcct tcgtggagct accgctggcc    960
agcattgtct cacttcatgc ctccagctgc ggtggtaggc tgcagacctc acccgcaccg   1020
atccagacca ctcctcccaa ggacacttgt agcccggagc tgctcatgtc cttgatccag   1080
acaaagtgtg ccgacgacgc catgaccctg gtactaaaga aagagcttgt cgcgcatttg   1140
aagtgcacca tcacgggcct gaccttctgg gaccccagct gtgaggcaga ggacaggggt   1200
gacaagtttg tcttgcgcag tgcttactcc agctgtggca tgcaggtgtc agcaagtatg   1260
atcagcaatg aggcggtggt caatatcctg tcgagctcat caccacagcg ggtgagatgg   1320
acagtcacgt gctaacccac ctggcccagg ggctgctgct gggccggggc ctcttcctgg   1380
cctgggaggg agcaggcctc gggaaactcc tggcaagcca tgtgtgtctg aatgcctcg    1440 gtctccccctt ctgtatgacc ggagcaggac tgctgagggt gacgctctcg gtctctcaag   1500
tcagagggct tagcacatac tggctgtgtg gccttgggca agtcacttta gttttctggg   1560
cccaaaggtg gcctaagaaa ggactctgcg ccacagggtg cttctgggca gccaatgagg   1620
tgctgtgtgg aagctcttca cacagcctgg cagctggtgc ctccttgata aatattagtt   1680
taa                                                                  1683

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
tggtcagcaa tgaggtgatc a                                               21

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
accgtccatc tcacccgaa                                                  19

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
cagtttcccg tcaggctcac cacc                                            24

<210> SEQ ID NO 8
<211> LENGTH: 34
<212> TYPE: DNA
<213> ORGANISM: Artificial Sequence
```

```
<220> FEATURE:
<223> OTHER INFORMATION: Synthetic Construct

<400> SEQUENCE: 8
ctcatcacca cagcggtaga gatggacagt cacg                          34

<210> SEQ ID NO 9
<211> LENGTH: 34
<212> TYPE: DNA
<213> ORGANISM: Artificial Sequence
<220> FEATURE:
<223> OTHER INFORMATION: Synthetic Construct

<400> SEQUENCE: 9
cgtgactgtc catctctacc gctgtggtga tgag                          34

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
tggtcagcaa tgaggtgatc a                                        21

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
accgtccatc tcacccgaa                                           19

<210> SEQ ID NO 12
<211> LENGTH: 29
<212> TYPE: DNA
<213> ORGANISM: Artificial Sequence
<220> FEATURE:
<223> OTHER INFORMATION: Synthetic Construct

<400> SEQUENCE: 12
cagtttcccg tcaggctcac cacctamra                                29
```